(12) United States Patent
Takaoka et al.

(10) Patent No.: US 7,623,907 B2
(45) Date of Patent: Nov. 24, 2009

(54) ENDOSCOPE FOR OBSERVING SCATTERED LIGHT FROM LIVING BODY TISSUE AND METHOD OF OBSERVING SCATTERED LIGHT FROM LIVING BODY TISSUE

(75) Inventors: Hideyuki Takaoka, Hino (JP); Mamoru Tamura, Sapporo (JP)

(73) Assignee: Olympus Corporation, Tokyo (JP)

( * ) Notice: Subject to any disclaimer, the term of this patent is extended or adjusted under 35 U.S.C. 154(b) by 708 days.

(21) Appl. No.: 10/896,950

(22) Filed: Jul. 23, 2004

(65) Prior Publication Data

US 2005/0054937 A1    Mar. 10, 2005

(30) Foreign Application Priority Data

Jul. 23, 2003    (JP) .............................. 2003-200304

(51) Int. Cl.
*A61B 6/00*    (2006.01)
(52) U.S. Cl. ................... 600/476; 600/101; 600/160; 600/178; 600/181; 600/182; 600/309; 600/310; 600/473; 600/474; 600/475; 600/477; 600/478; 600/479; 600/480; 356/39; 73/865.5; 250/222.2
(58) Field of Classification Search ............... 600/407, 600/473–480, 101, 160, 178, 181, 182, 309, 600/310; 356/335–337, 340, 342, 39; 73/865.5; 250/222.2
See application file for complete search history.

(56) References Cited

U.S. PATENT DOCUMENTS

| 2,816,479 | A | * | 12/1957 | Sloan ......................... 356/336 |
| 4,387,993 | A | * | 6/1983 | Adrian ....................... 356/336 |
| 4,537,507 | A | * | 8/1985 | Hess .......................... 356/336 |
| 5,164,787 | A | * | 11/1992 | Igushi et al. ................. 356/336 |
| 5,199,431 | A | * | 4/1993 | Kittrell et al. ............... 600/477 |
| 5,815,264 | A | * | 9/1998 | Reed et al. .................. 356/336 |
| 6,091,984 | A | * | 7/2000 | Perelman et al. ............ 600/476 |
| 6,177,994 | B1 | * | 1/2001 | Watson et al. ............... 356/343 |

FOREIGN PATENT DOCUMENTS

WO        WO 00/43750    *    7/2000

* cited by examiner

*Primary Examiner*—Brian Casler
*Assistant Examiner*—James Kish
(74) *Attorney, Agent, or Firm*—Arnold International; Bruce Y. Arnold

(57) ABSTRACT

An endoscope apparatus and method are disclosed wherein first and second light beams, each having different center wavelengths, illuminate an object. A detector and a light receiver optical system are provided that receive back-scattered light from first and second illumination devices. A processor is provided that calculates a value corresponding to the size of particles that back-scatter light of the first and second light beams that are incident onto the object, with the calculated value being independent of the concentration of the particles. The first illumination device and the second illumination device are arranged in a specified manner so that a specified condition is satisfied.

26 Claims, 14 Drawing Sheets

ENDOSCOPE FOR OBSERVING SCATTERED LIGHT FROM LIVING BODY TISSUE AND METHOD OF OBSERVING SCATTERED LIGHT FROM LIVING BODY TISSUE

This application claims benefit of priority from JP 2003-200304 filed on Jul. 23, 2003, the subject matter of which is hereby incorporated by reference.

BACKGROUND OF THE INVENTION

Technology for observing and collecting information about cells and living body tissue by detecting scattered light from a living body when light is illuminated onto the cells of living body tissue is already known. For example, International Patent Publication WO 00/43750, discloses a system for measuring the size distribution of cell nuclei in a living tissue by detecting the back-scattered light from the living tissue in different directions and for making visible the abnormality of the cells by displaying the scattered light on a display device.

In summary, in the system, a living tissue is irradiated by illumination light and the spectral intensity distribution of the scattered light from the living tissue is detected. This enables one to determine information regarding particles in the living tissue, such as the diameter and the refractive index of the particles. It is known that the nuclei of cancerous cells are larger in size than the nuclei of normal cells. Therefore, by measuring the back-scattering characteristics of the light that is scattered by the living tissue, one can predict whether the cells that scatter the light are cancerous or normal.

The scattered light from living body tissue includes both single scattering components and multiple scattering components. Since information of interest relating to the particles is included primarily in the single scattering components, it is desirable to remove the multiple scattering components. As one method of doing this, the scattered light is detected at multiple angles, and a calculation is made of the scattered light intensity between these angles.

In the prior art example mentioned above, as a specific construction for accomplishing detection at multiple scattering angles, an explanation is provided of an example which uses a single illumination optical system and multiple detection optical systems. If the detection optical system is multiple, then—particularly in the case of observing the scattering spectrum information with an endoscope—, the size of the front part of the endoscope becomes large.

BRIEF SUMMARY OF THE INVENTION

The present invention relates to an endoscope for observing scattered light from a living body tissue, more particularly, back-scattering from a living body tissue, and an observation method using the same. The invention enables the detection optical system to be simplified while providing a front end portion that is relatively small.

BRIEF DESCRIPTION OF THE DRAWINGS

The present invention will become more fully understood from the detailed description given below and the accompanying drawings, which are given by way of illustration only and thus are not limitative of the present invention, wherein.

DETAILED DESCRIPTION

First, an explanation will be provided of the principles of observing the state of cells using the present invention.

Measurements of information can be made concerning a particle (such as the average particle diameter, the index of refraction, and the like) by detecting back-scattered light from the particle. For example, given that the diameter of cell nuclei are different between cancerous cells versus normal cells, by measuring the back-scattered light caused by cell nuclei of tissue of a living body, differentiation (i.e., diagnosis) of cancer cells versus normal cells can be accomplished. Through such observations, using a relatively simple construction, differentiation can be made between healthy cells and cancerous cells without causing injury to the living body tissue.

Also, in obtaining the information concerning the particles (e.g., the size of the cell nuclei), it is desirable to measure the single scattering events of the particles. However, included in the returned light (i.e., the illumination light that has been scattered by the living body tissue and detected), are both single-scattering-event components and multiple-scattering-event components. The multiple scattering light components have been scattered by multiple particles and constitute noise. In addition, the multiple scattered light components constitute a large share of the returned light. Therefore, it is necessary to obtain only the single scattering light components by removing the multiple scattering light components from the returned light.

Figure 11:
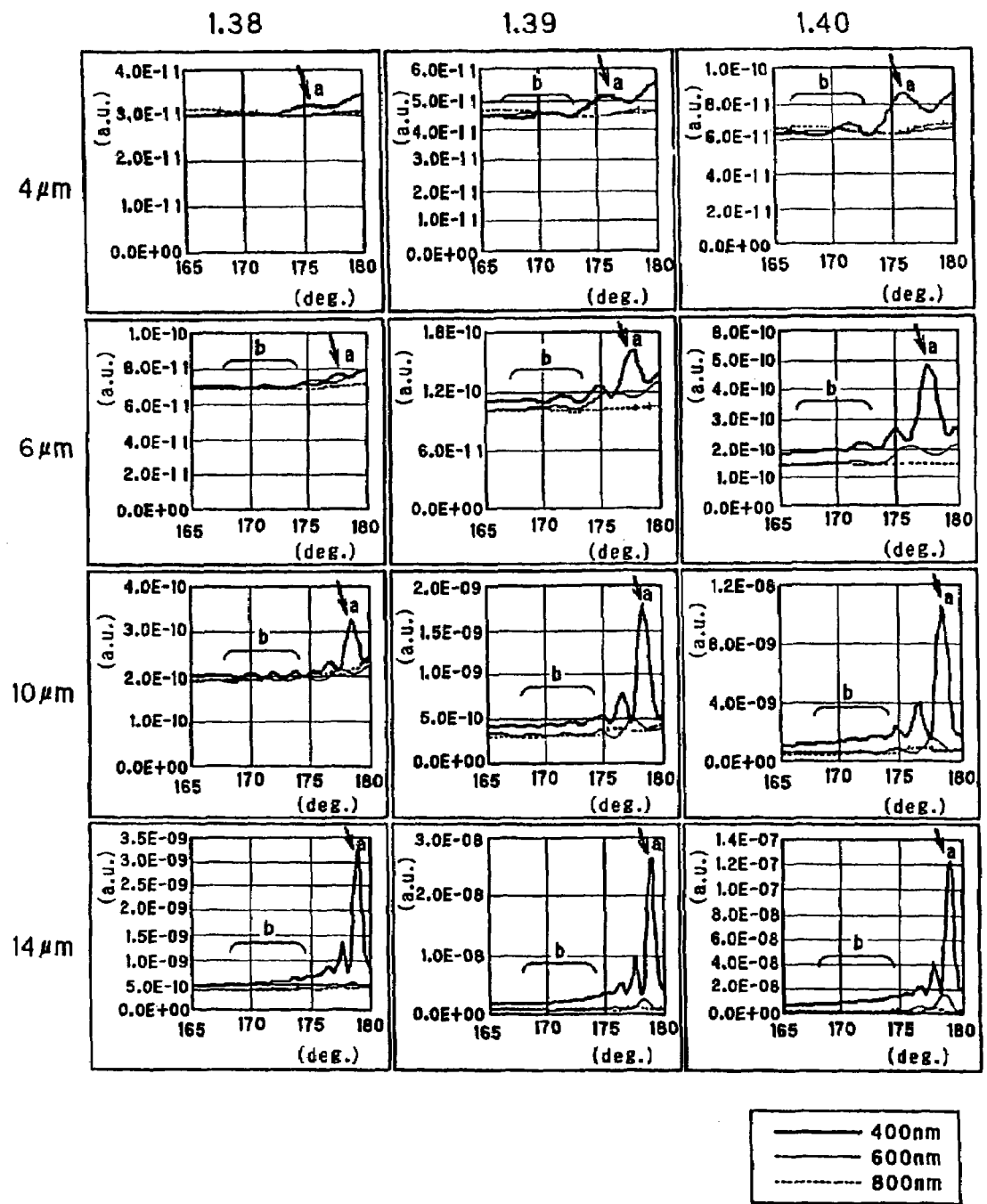
FIG. 11 is a diagram showing, for light at three different wavelengths, twelve calculated graphs of the back-scattered light intensity in arbitrary units (a. u.) as a function of the scattering angle (in degrees, deg.) for spherical particles having four different average diameters and three different refractive indexes.

FIG. 11 shows, for light of three different wavelengths, twelve different graphs that result from calculating the back-scattered light intensity (in arbitrary units) as a function of the scattering angle (in degrees) by spherical particles, based on the Mie Scattering Theory. The average values of the granular diameters shown in these graphs are 4 μm, 6 μm, 10 μm, and 14 μm, whereas the index of refraction of the particles is 1.38, 1.39, and 1.40. The index of refraction of the material surrounding the particles is 1.33. An "E" in the data of FIG. 11, as well as in other figures, indicates that the number following the "E" is the exponent to the base 10. For example, "1.0E-2" represents the number $1.0 \times 10^{-2}$. The twelve graphs are shown in four rows and three columns. The graphs in a given row show the back-scattered light for particles having the same diameter but different refractive indexes, with the particle diameter being listed to the left of each row of graphs. The graphs in a given column are for scattering by particles having the same refractive index, with the refractive index being listed above each column of graphs. Each graph shows the back-scattered light intensity per particle as a function of the scattering angle.

In these graphs, variations in the particle diameter are assumed to follow a Gaussian distribution, and the value listed to the left of each row is the average particle diameter. In addition, concerning the graphs in the upper two rows having an average particle diameter of 4 μm and 6 μm, respectively, the standard deviation of the particle diameters is 1 μm. On the other hand, concerning the graphs in the lower two rows having an average particle diameter of 10 μm and 14 μm, respectively, the standard deviation of the particle diameters is 1.5 μm. Thus, the scattering intensity shown in each graph is the average scattering intensity per particle. The back-scattered light intensity (on the Y-axis) is plotted for each of the graphs in FIG. 11 as a function of the scattering angle (on the X-axis).

In each graph of FIG. 11, an arrow 'a' points to the peak scattering intensity that occurs in the scattering angle range of 175°-180°. On the other hand, in all but one of the graphs of FIG. 11, a region 'b' is shown wherein the scattering angle is 175° or less and the scattering intensity as a function of the scattering angle remains relatively unchanged. This is true for all particle 25 diameters, for all particle indexes of refraction, and for all the incident light wavelengths illustrated in FIG. 11. In addition, the larger the particle diameter, the larger is the ratio of the peak scattering intensity 'a' that occurs in the scattering angle range of 176°-180° divided by the scattering intensity in the region 'b'.

In each graph, three scattering intensities are shown. The scattering shown using a thick solid line is for incident light having a wavelength of 400 nm, the scattering shown using a thin solid line is for incident light having a wavelength of 600 nm, and the scattering shown using a dotted line is for incident light having a wavelength of 800 nm.

Figure 12:
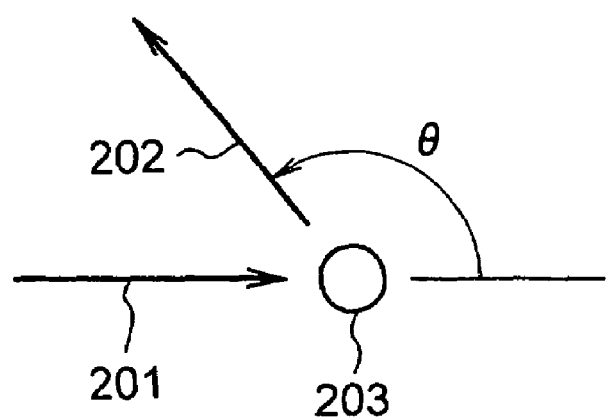
FIG. 12 is a diagram for explaining the manner in which the scattering angle $\theta$ is measured.

FIG. 12 illustrates the manner in which the scattering angle θ is measured. As is apparent from FIG. 12, the scattering angle θ for the scattered ray 202 is measured from the direction of propagation of a light ray 201 that is incident onto a particle 203.

Figure 13:
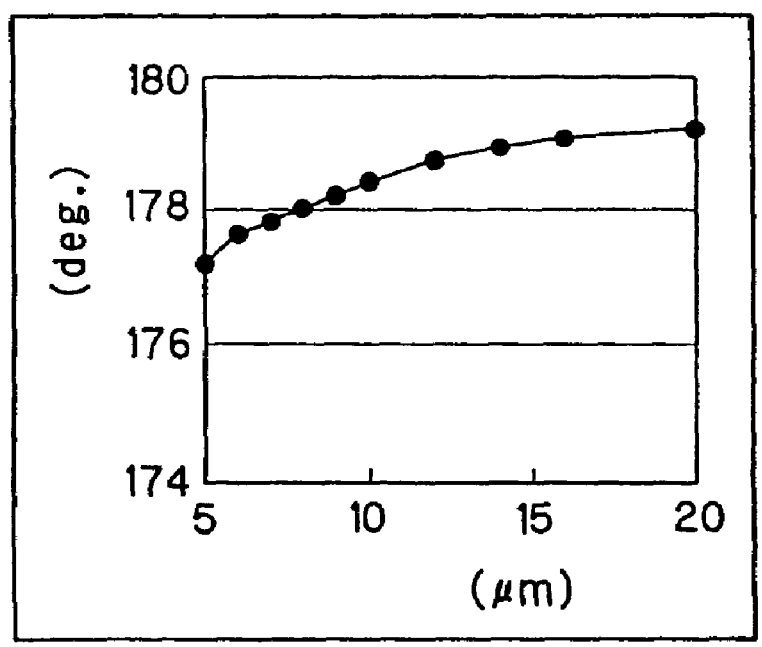
FIG. 13 is a graph which plots the angle of maximum back-scatter (on the Y-axis) versus the average particle diameter (on the X-axis)

FIG. 13 is a graph showing the maximum back-scattering angle of the light having a wavelength of 400 nm in degrees (Y-axis) versus the particle diameter in μm (X-axis) for the situation where the index of refraction of the particles is 1.39.

For illumination light having a wavelength of 400 nm that is incident, for example, onto a test material which includes spherical particles, the back-scattered light can be detected. As mentioned above, the back-scattered light includes single scattering components and multiple scattering components. In this instance, the single scattering light component is light that has been scattered from the surface of the test material. On the other hand the multiple scattering light component is light that has been scattered by particles deeper within the test material than particles at the surface of the test material.

With the present invention, a first scattering angle range is established at 176°-180°, and a second scattering angle range is established at 176° or less. The light that is back-scattered from an object is detected within the respective first and second ranges of scattering angles. Because the multiple scattering light component has been repeatedly scattered within the living body tissue, the angular distribution of the back-scattered light from this component is uniform. Thus, within the first scattering angle range and within the second scattering angle range there is little difference in the intensity of the back-scattered light from this component.

On the other hand, for the single scattering light component, differences in the relative scattering intensity occur within the range of the first scattering angle and the second scattering angle. These differences relate to the size of the particles that cause the light to be scattered. Therefore, by calculating the difference between a first signal being output from a detector when the object is illuminated by the first illumination device versus a second signal being output from the detector when the object is illuminated by the second illumination device, or by calculating a ratio of the first signal divided by the second signal, the noise component caused by the multiple scattering light components can be eliminated from the detected back-scattered light signal. As a result, a scattering signal can be extracted that corresponds in intensity to substantially only the single scattering light component. When the scattering particles within the test material are large in size, then the difference in these detected signals, and a ratio of these two signals becomes large and enables information relating to the scattering particles to be obtained. By comparing the results of the above measurements with scattering results produced by different materials for which the sizes of the scattering particles are known, the size of the scattering particles of the living test sample can be estimated.

Of course, the angular ranges at which the scattered light is detected need not be limited to the specific ranges given above, or limited to only two angular ranges. Clearly, the scattering intensities can be measured at multiple angles. In addition, observations may also be made using illumination lights that have different wavelengths, or by using a single illumination light source for which the emission wavelength(s) may be varied.

Moreover, in the cells of living body tissue, the cell nuclei of normal cells generally have a diameter in the range of 4 μm-7 μm. On the other hand, abnormal cells tend to have larger cell nuclei with diameters in the range of 9 μm-20 μm. As a result, the number of cell nuclei per unit area decreases in the case of abnormal cells. In addition, the back-scattered light is influenced by other cell properties. For example, the ratio of the index of refraction of the cell nucleus divided by the index of refraction (1.33) of the cytoplasm is known to be in the range of 1.035-1.05. By using this knowledge, simulations can be made of the back-scattered light when a selected wavelength of light in the visible wavelength region illuminates the object surface of a living body tissue. For example, each of the graphs of back-scattered light in FIG. 11 is computed for specified illumination conditions, particle sizes, indexes of refraction, and illumination wavelengths.

Furthermore, for such observations, it is desirable that the wavelength of the light from the light source be 500 nm or shorter. In a scattering body, and particularly in the case where back-scattering by cell nuclei is a primary source of the scattering, as shown in FIG. 11, changes in the scattering angle relative to the size of the scattering particle occur when the wavelength of the illumination light source is short. Therefore, it is desirable to use a wavelength of 500 nm or shorter, which is on the short wavelength side of the visible region.

In addition, in the case of making observations by changing the wavelength of the illumination light, it is desirable to use wavelengths of 500 nm or shorter, as well as to use wavelengths of 500 nm or longer.

In the case where there is considerable variation in the concentration of the scattering particles included in the sample, the scattering intensity changes according to the number of particles in the region where the scattering occurs. Therefore, in the present invention, it is desirable that there be multiple wavelengths of light which illuminate the scattering body. If this is the case, then a scattering signal can be obtained that is predictive of the particle diameter and which does not vary with the concentration of the particles. For example, in the examples shown in FIG. 11, for rearward scattered illumination having a wavelength of 600 nm, the difference in the intensity of the illumination for different scattering angles is less than that for rearward scattered illumination having a wavelength of 500 nm or shorter. Therefore, the intensity of the back-scattered light having a wavelength of, for example, 400 nm divided by the intensity of the back-scattered light having a wavelength of 600 nm is obtained over a first range of scattering angles and over a second range of scattering angles. By comparing these ratios of scattering intensities, a signal can be obtained that corresponds to the size of the particles and that is independent of the number of particles that are illuminated (i.e., the particle concentration).

Figure 1:
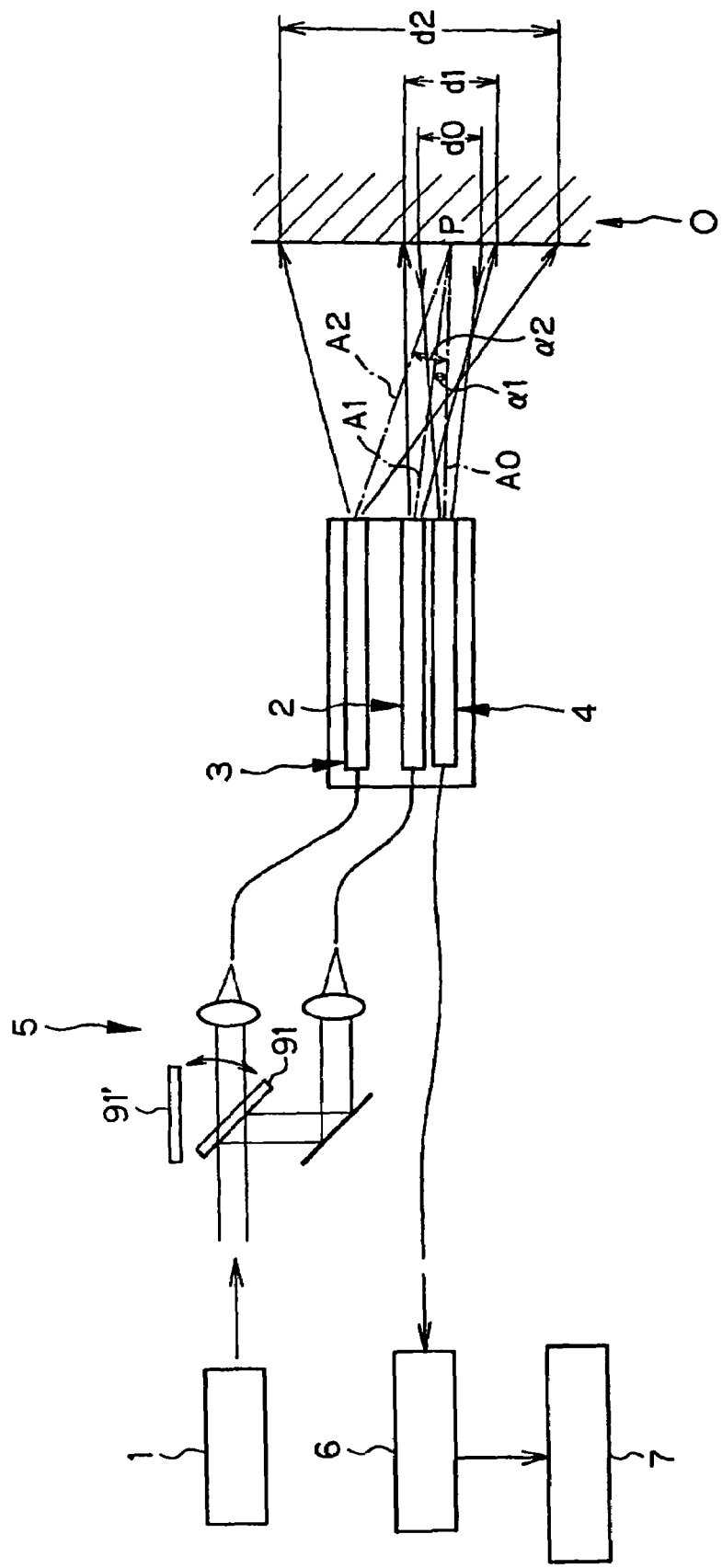
FIG. 1 shows the overall construction according to Embodiment 1 of an endoscope used for obtaining the back-scatter intensity as a function of scattering angle (herein termed the 'back-scattering characteristics') of an object such as living body tissue according to the present invention.

The construction of an embodiment of an endoscope apparatus that may be used for practicing a method according to the present invention is shown in FIG. 1. In FIG. 1, a light source 1 is provided. The illumination from the light source may be selectively directed via an optical switch 5 to either a first illumination device 2 or a second illumination device 3, each of which is formed of a light conducting body such as an optical fiber. From the front ends of the first illumination device 2 and the second illumination device 3, illumination light is emitted so as to be incident onto an object O, such as living body tissue. Light that is scattered by the object O is received at one end of a light receiver optical system 4 formed of a light conducting body such as an optical fiber, and the received light is led to, and detected by a detector 6. The detected signal is then input to a processor 7, and the difference or ratio of the two detected signals at the time of illumination by a first illumination device 2 versus at the time of illumination by a second illumination device 3 is calculated by the processor 7.

The first illumination device and the second illumination device may be arranged relative to the optical axis of the light receiver optical system such that the following Condition (1) is satisfied:

$$\alpha 1 < \alpha 2 \qquad \text{Condition (1)}$$

where

α1 is the angle formed by the optical axis of the light receiver optical system and a line which is substantially in the center of the illumination light beam that is emitted from the first illumination device and which intersect at a point where the optical axis of the light receiver optical system intersects the surface of the sample; and α2 is the angle formed by the optical axis of the light receiver optical system and a line which is substantially in the center of the illumination light beam that is emitted from the second illumination device and which intersect at a point where the optical axis of the light receiver optical system intersects the surface of the sample.

If the numerical aperture of the light conducting body is 0.3 or less, then the angle of the received back-scattered light can be restricted, and background noise can be desirably reduced at the time of detection.

Referring to FIG. 1, which illustrates Embodiment 1 but is also generally well-representative of the invention in general, it is desirable that the illuminated areas have the ranges d0, d1 and d2. The range d2 includes within it the area having the range d1 and the area having the range d0, where range d2 is the region on the surface of the object O that is illuminated by the second illumination device, range d1 is the region on the surface of the object O that is illuminated by the first illumination device, and range d0 is the region on the surface of the object O that corresponds to the field of view of the light receiver optical system 4. Furthermore, it is also desirable that the range d1 includes within it the range d0. By constructing the first illumination device 2 and the second illumination device 3 in this manner, more reliable results are achieved and regions of interest on the object O can be visually observed by means of the illumination from the second illumination device 3.

As shown in FIG. 1, a mirror 91 that may be controllably inserted into and removed from the light path can serve as the optical switch 5. When the mirror 91 is in the position 91' light from the light source is led to the second illumination device 3, and when it is inserted into the light path, light from the light source is led to the first illumination device 2. Of course, other known mechanisms for switching the optical path can be used.

In addition, in order to perform accurate measurements, it is desirable that the detection intensities of the scattered light be correctly calibrated to correspond to the respective first illumination device and second illumination device, as discussed below.

Prior to measuring back-scattered light from an object, light intensities R1 and R2 scattered by a standard body such as a white scattering plate that is illuminated by the first illumination device and the second illumination device are pre-measured, respectively. In measuring back-scattered light from the object, the optical scattering intensity while using the illumination of the respective first illumination device and the second illumination device is S1 and S2, respectively. Using a processor, by calculating the difference or ratio of S1/R1 and S2/R2, accurate measurements can be made even in the case where there is a strong difference generated in the illumination of the two illumination devices.

In addition, in the case of performing observations with a high signal-to-noise S/N ratio, it is necessary that the measurements be taken a number of times, or over an extended period of time. In the case where the object is a living body, since the object usually moves due to the activities of the living body (including breathing and pulse), it is possible that the measurement environment or measurement conditions may be different at the time of measurement using the first illumination device versus at the time of measurement using the second illumination device. In this case, there is concern that the S/N ratio of the signal may drop, making it difficult to obtain accurate measurements. In addition, in the case where the output intensity of the light source is insufficiently stable, accurate measurements may be difficult to obtain. Therefore, by switching the first illumination device and the second illumination device continuously and repetitively over a sufficiently short period of time, while comparing the changes in the object or changes in the output of the light source, measurements become possible without the influence of these changes. In addition, by performing calculations using a processor in which there is synchronization while continuously switching the illumination, measurement can be made with a high time resolution without the influence of these changes.

Various embodiments of the invention will now be discussed in detail with reference to the drawings.

EMBODIMENT 1

FIG. 1, which illustrates Embodiment 1 of an endoscope for observing scattered light from an object such as living body tissue, has already been discussed above in discussing the invention in general terms, and will not be further described except to note that Embodiment 1 is characterized by having the above Condition (1) satisfied.

In this case, the first illumination device and the second illumination device should be arranged relative to the light receiver optical system so that the area on the object illuminated by the first illumination device includes the field of view of the light receiver optical system, and the area of the object illuminated by the second illumination device includes the area of the object illuminated by the first illumination device.

It is desirable that the first illumination device and the second illumination device be arranged relative to the light receiver optical system so that the angle formed by the illumination light at the time of illumination by the first illumination device and the scattered light detected from the object by the light receiver optical system, that is, the angle 180° minus $\alpha 1$, is within the range of 176°-180°, and that the angle of the illumination light that is incident onto the object at the time of illumination by the second illumination device and the scattered light detected from the object with the light receiver optical system, that is, the angle 180° minus $\alpha 2$, is less than or equal to 176°.

Also, it is desirable that there be provided an objective optical system and an image detector, such as a CCD, arranged at the image surface of the objective optical system so that an observer can observe detected images of the object.

The first illumination device and the light receiver optical system may be constructed so that a common optical axis is shared by these components. In addition, the first illumination device and the light receiver optical system may be constructed so as to be movable in the space between the object and the second illumination device. It is also possible that the second illumination device serves as an illumination device that enables the object to be observed as color image.

It would also be acceptable for there to be a construction which provides a light source in which light from the light source is continuously switched so as to be led to either the first illumination device or the second illumination device.

In addition, it is desirable that the illumination light from the first illumination device and from the second illumination device each have wavelengths of 500 nm or shorter.

As the illumination light from the first illumination device and from the second illumination device, use is made of two selected bands within the visible wavelength region, and a processor is used to eliminate noise components in the signal of interest. More specifically, the difference between the signal detected of light of wavelength 500 nm or shorter from the first illumination device at the time of illumination by the first illumination device versus the signal detected of light of wavelength 500 nm or shorter from the second illumination device at the time of illumination by the second illumination device is made to be the difference signal I. Using a narrow bandwidth light having a center wavelength of 500 nm or greater that illuminates the object, the difference between the signal having a center wavelength of 500 nm or greater that is detected at the time of illumination by the first illumination device versus the signal detected of light having a center wavelength of 500 nm or greater at the time of illumination by the second illumination device is made to be the difference signal II. Calculations are accomplished of the difference or the ratio of these two signals I and II by the processor.

The light receiver optical system is also provided with a collimator optical system. In addition, the first illumination device and the light receiver optical system may also be constructed using the same collimator optical system. In addition, the first illumination device and the second illumination device may each be formed of light emitting devices LEDs.

EMBODIMENT 2

Figure 2:
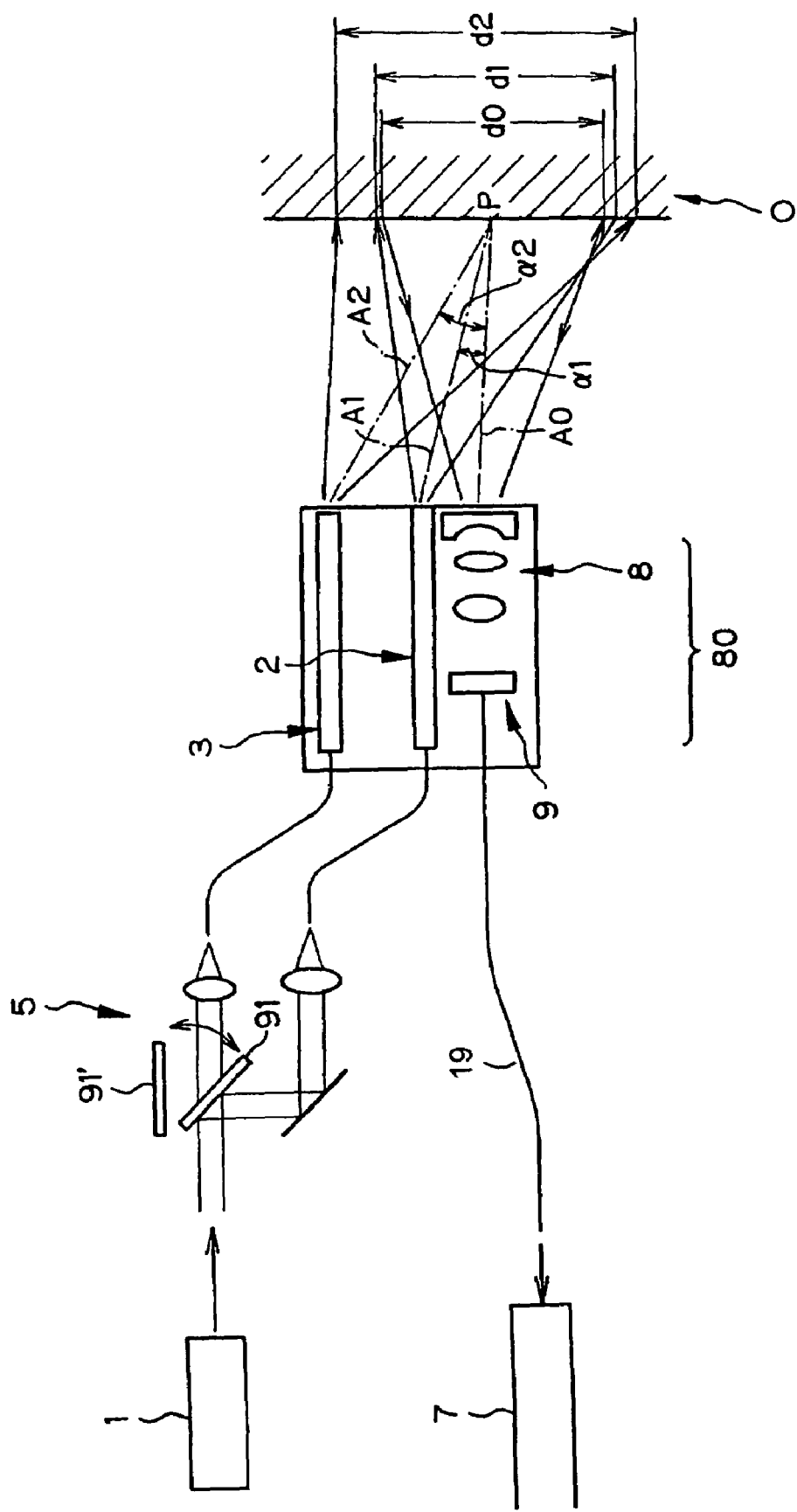
FIG. 2 shows the overall construction according to Embodiment 2 of an endoscope used for obtaining the back-scattering characteristics of an object such as living body tissue according to the present invention.

FIG. 2 shows the construction of an endoscope for observing scattered light from an object, such as living body tissue, according to Embodiment 2. In this embodiment, an objective optical system 8 is used in lieu of the light receiver optical system 4 within the insertable portion of the endoscope. In other words, in this embodiment, rather than merely receiving light that is detected, images of the object are formed by a lens system onto a light receiver surface of an image detector 9, such as a CCD. Illumination light from the light source 1 passes through the optical switch 5, and is selectively led to the first illumination device 2 or to the second illumination device 3, each of which is formed of a light guiding body such as an optical fiber. From the front ends of the first illumination device 2 and the second illumination device 3, the illumination light is emitted onto an object O such as living body tissue. The image created by the light that has been back-scattered by the object O is formed by the objective optical system 8 as in the case of using an endoscope objective lens, and this image is then detected by the image detector 9 and converted into an electrical output that constitutes an image signal. The image signal is input to the processor 7, and the difference or ratio of the image signal passing through the objective optical system 8 at the time of illumination by the first illumination device 2 and of being detected by the image detector 9, and the image signal passing through the objective optical system 8 at the time of illumination by the second illumination device 3 and of being detected by the image detector 9 is calculated by the processor 7.

In this embodiment as well, the above Condition (1) as discussed for Embodiment 1 is satisfied.

Just as in Embodiment 1, a major advantage of the construction of this embodiment is having a plurality of illumination devices. This enables the illumination angles at a position P of the object to be different relative to the imaging unit 80 that is formed of the objective optical system 8 and the image detector 9. When, for example, such a construction is built into an endoscope, the image detector 9, such as a CCD and the like that is arranged in the insertable part of the endoscope can be used both for measurement and for observation, and no detector for measurement purposes only is needed. In addition, the optical path of the light source is split outside of the endoscope insertable part, and the two resulting light beams are directed to the object by optical fibers arranged in the insertable part of the endoscope. Thus, the endoscope front end may be small in diameter.

Just as in Embodiment 1, it is desirable that range d2 includes within it the area having the range d1 and the area having the range d0, where d2 is the region on the surface of the object O that is illuminated by the second illumination device 3, d1 is the region on the surface of the object O that is illuminated by the first illumination device, and d0 is the region on the surface of the object O that corresponds to the field of view of the objective optical system 8. Furthermore, it is again also desirable that the range d1 includes within it the range d0. By such a construction, visual observation of the state of the object using the second illumination device 3 can be made through the objective optical system 8 and the imaging element 9.

Figure 3B:
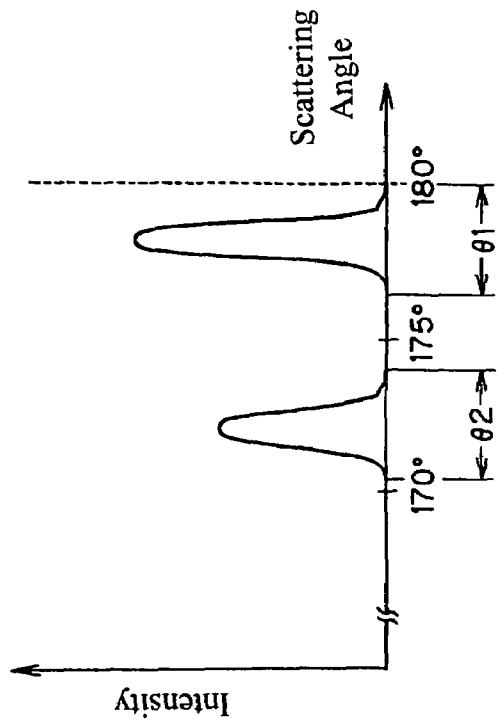
FIG. 3(b) shows the back-scattering characteristics (i.e., the back-scattered intensity as a function of scattering angle) of back-scattered illumination light obtained by the light receiver optical system when the illumination light is switched between the two illumination systems shown in FIG. 3(a)

Next, an explanation will be provided of the endoscope and method of observation used for back-scattered light observation of an object such as living body tissue according to the Embodiment 3. FIG. 3(*a*) shows the construction of the essential components of an endoscope used for back-scattered light observation of living body tissue very similar to Embodiment 1. This figure shows a slightly modified structure from that of Embodiment 1 in the construction of the insertable part of the endoscope shown in FIG. 1. Although the endoscope here discussed includes an optical switch 5, a detector 6, and a processor 7, these are identical to those shown in FIG. 1 and will not be further discussed.

In this embodiment, in the endoscope front end 10, there are arranged the first illumination device 2, the second illumination device 3, and the light receiver optical system 4. A front end hood 11 is attached to the endoscope front end 10 and functions to keep a fixed distance between the object and the endoscope front end 10, and thus the detection angles $\theta 1$ and $\theta 2$ for the scattered light are maintained in a fixed range.

Also, the first illumination device 2 includes the optical fiber 21 and a positive lens 22 arranged at the front end of the optical fiber 21, and the second illumination device 3 includes the optical fiber bundle 31 and a negative lens 32 arranged at the front end of the optical fiber bundle 31. As shown in FIG. 3(*a*). the positive lens 22 is laterally offset from the optical axis of the light output from the optical fiber 21. and the negative lens 32 is laterally offset from the optical axis of the light output from the optical fiber bundle 31. thereby causing the light output from each of the first illumination device 2 and the second illumination device 3 to be refracted transversely. Using two laterally offset lenses in this manner enables the center ray of light from each of the first illumination device 2 and the second illumination device 3 to intersect the optical axis of the light receiver optical system 4 at substantially the same point while also satisfying Condition (1). The light receiver optical system 4 includes optical fiber 41 and a positive lens 42 arranged at its front end.

Referring to FIG. 3(*a*), light that has been back-scattered by an object O is measured relative to a transmitted center ray of a first illumination device 2, that is, the center ray of the illumination light beam that is emitted from the first illumination device 2 and is incident on the intersecting point of the object O and the optical axis of the light receiver optical system 4. Likewise light that has been back-scattered by the object O is measured relative to a transmitted center ray (the center ray of the illumination light beam which is emitted from the first illumination device of a second illumination device 3 and is incident on the intersecting point of the object O and the optical axis of the light receiver optical system 4). In each case, the scattering angle $\theta$ is measured relative to the center ray that would be transmitted, discussed previously with regard to FIG. 12. In FIG. 3(*a*), the arrow labeled $\theta 1$ illustrates the reference point for measuring the scattering angle for light from the first illumination device 2 as well as the direction of the measurement. Likewise, in the same figure, $\theta 2$ illustrates the reference point for measuring the scattering angle for light from the second illumination device 3. When the detected scattered light that enters the light receiver optical system 4 is then plotted for the two illumination devices onto a single graph, the graph of FIG. 3(*b*) is obtained, wherein the ordinate (the Y-axis) shows the scattered light intensity and the abscissa (the X-axis) shows the scattering angle, measured in each case relative to the illumination source center ray, as shown in FIG. 3(*a*). As can be seen, the detected light within the scattering angles in the range of $\theta 1$ from the first illumination device 2 lies in the approximate range of 176°-180°, and the detected light within the scattering angles in the range $\theta 2$ from the second illumination device 3 lies in the approximate range of 170°-174°. Thus the distribution range of $\theta 2$ is included in the range of 176° or less. Also, the actual light intensity detected by the detector 6 when the sample is illuminated by the first illumination device 2 is a value obtained by integrating the right side peak in FIG. 3(*b*) with respect to detection time (i.e., accumulating the value of the right side peak intensity in FIG. 3(*b*) during the time period of detection), and in the case of illumination by the second illumination device 3, the peak distribution of the left side of FIG. 3(*b*) is a value obtained by integrating the left side peak in FIG. 3(*b*) with respect to detection time. By calculating the difference or ratio of the accumulated values using a processor 7, the size can be specified of the epithelial cell nuclei of the living body tissue from the back-scattering measurement ranges $\theta 1$, $\theta 2$ shown in FIG. 3(*a*). By this means, a diagnostic method for differentiating between normal cells and cancerous cells of living body tissue can be provided using an endoscope, without cutting the tissue of the object.

As noted above, when $\theta 1$ is in the range of 176°-180° and $\theta 2$ is in the range of 176 degrees or less, the determination of the size of the nucleus becomes easier.

In this case, it is also desirable that the illumination light from the first illumination device and the second illumination device have a wavelength of 500 nm or shorter.

In addition, it is also desirable that the first illumination device and the second illumination device be arranged relative to the objective optical system and the object so that the illuminated region with the first illumination device illuminating the object includes the view field of the objective optical system, and that the illuminated region with the second illumination device illuminating the object includes the region of the object illuminated by the first illumination device.

The second. illumination device may be combined with an illumination means for observing the object surface and an area peripheral to the object surface. Also, a light source may be provided in which multiple wavelength selective filters are arranged to be freely inserted into and removed from the optical path, and the light source in turn may also be provided, at a minimum, with a mode which forms the narrow bandwidth illumination light of the visible wavelength regions used in the back-scatter observations of the object surface, and a mode which produces successive illumination lights of blue (B), green (G), and red (R) colors, as well as a mode for generating white light.

With a light source which arranges multiple wavelength selective filters so as to be freely insertable into and removable from the light path by changing the assembly of the wavelength selective filters, construction may be accomplished whereby it is possible to switch between a mode which generates the narrow bandwidth illumination light of the visible wavelength region used in the back-scattered light observations of the object surface, a mode which generates, in repeated sequential order, illumination lights of blue (B), green (G), and red (R) colors used in the observation of the object surface and the area peripheral to the object surface, and a mode which generates white illumination light.

Figure 4B:
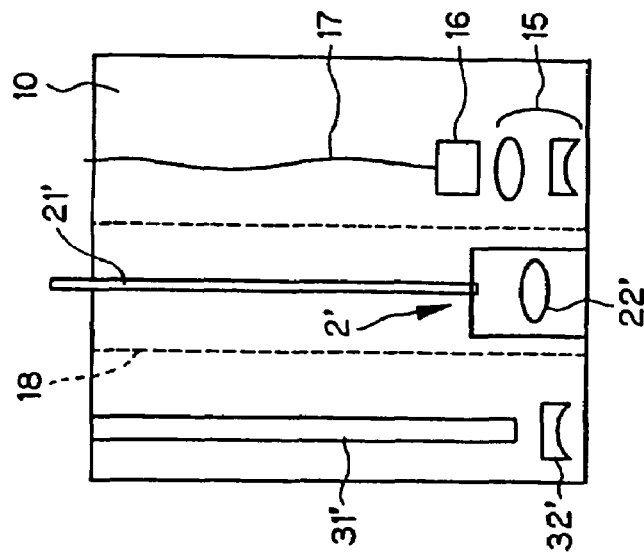
FIG. 4(b) shows a possible modification of the structure shown in FIG. 4(a)
Figure 4A:
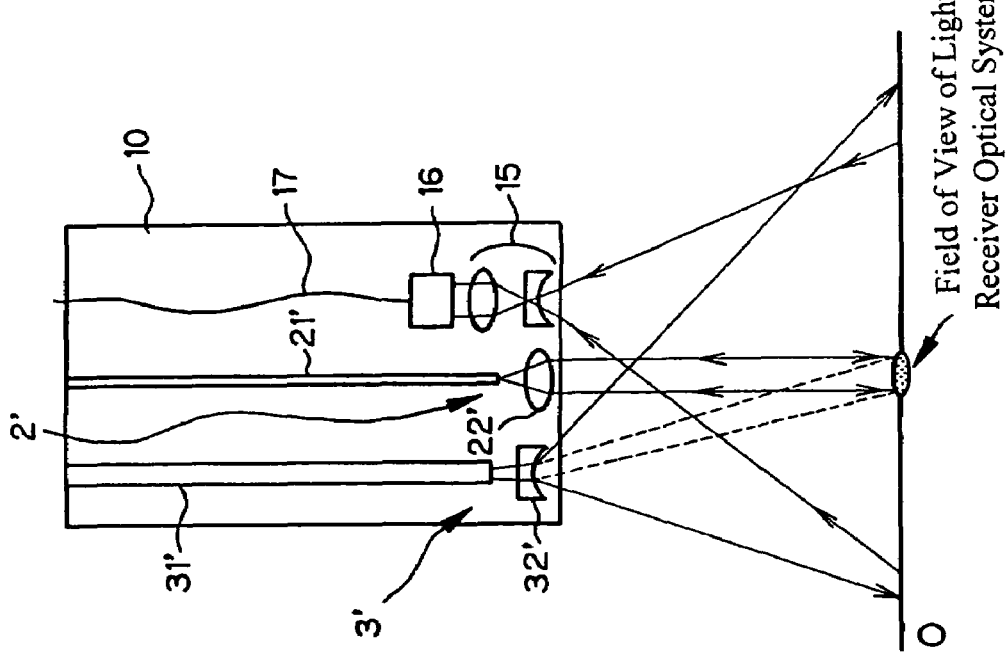
FIG. 4(a) shows the construction of some of the essential components (including two illumination systems and a light receiver optical system) of the endoscope used for obtaining the back-scattering characteristics of an object such as living body tissue as Embodiment 4.

Concerning Embodiment 4 according to the present invention, an explanation will now be provided with reference to FIGS. 4(a) and 4(b).

Figure 3A:
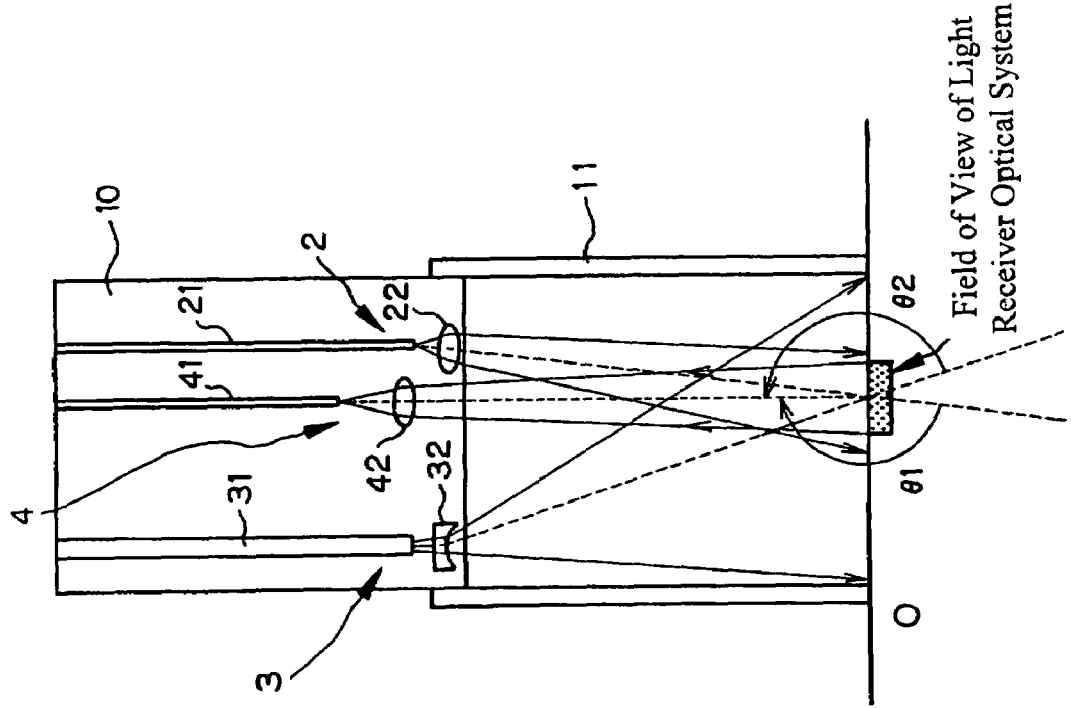
FIG. 3(a) shows the construction of some of the essential components (including the two illumination systems and a light receiver optical system) of the endoscope used for obtaining the back-scattering characteristics of an object such as living body tissue as Embodiment 3.

FIG. 4(a) shows the construction of the essential elements of Embodiment 4, which are similar in most respects to Embodiment 3 shown in FIG. 3(a). The construction of the following components in this embodiment are the same as in Embodiment 1: the light source 1, the optical switch 5, the detector 6, and the processor 7. Thus, further explanation of these components will be omitted here. However, the first and second illumination devices and the light receiver optical system in this embodiment are different. In FIG. 4(a), 2' serves the combined function of being the first illumination device as well as the light receiver optical system. Also, 3' serves the combined function of being the second illumination device as well as an optical system for illumination for obtaining observations of color images of the object.

More specifically, in the front part of the endoscope 10 are arranged the combined first illumination device/light receiver optical system 2' and the combined second illumination device/illumination optical system 3'. The combined first illumination device/light receiver optical system 2' is arranged so that a collimator optical system 22' having positive optical power collimates the light emitted from the end of the optical fiber 21' and directs it to the object. The collimator optical system 22' also functions as a light condenser that directs the back-scattered light from the illuminated object back into the optical fiber 21'. The combined second illumination device/ illumination optical system used for color image observation 3' is formed of a lens 32' that is arranged in front of the end of the optical fiber 31' so as to receive the illumination emitted by the optical fiber 31' and direct it to the object.

The illumination light from the light source 1 transits the combined first illumination device/light receiver optical system 2' when directed by the optical switch 5 where the light is selectively directed to the rear end of the optical fiber 21'. It then transits the collimator optical system 22' located at the front end of the endoscope. The collimated illumination light is then illuminated onto object O. Light scattered by the object O is received by the same collimator optical system 22', and passes a reverse optical path so as to reach the rear end of the optical fiber 21'. The light emitted by the rear end of the optical fiber 21' is then directed to a detector 6 by separating it from the illumination light by a beam splitter (not shown) or the circulator of Embodiment 8 as will be explained later.

In the endoscope front end 10, in addition to there being the components 2' and 3' as discussed above, an image detector 16 such as a CCD is arranged at the image surface of an objective optical system 15 that is used for color image observation. An image signal from the image detector 16 is sent to an image processor and monitor, not shown in the drawings, using a signal line 17, and is used to produce an image as displayed by an ordinary electronic endoscope observation device.

In this embodiment, the illumination range d2 of the combined second illumination device/illumination optical system 3' used for color image observations is constructed so as to conform with or include the observation range of the objective optical system 15 and the image pickup device 16. Observations as performed with a conventional endoscope are accomplished using illumination from the combined second illumination device/illumination optical system 3'. Collimated illumination light from the combined first illumination device/light receiver optical system 2' is illuminated onto an area of the surface of the object, which is selected during the color image observation, and measurements are performed in the first scattering angle range using the combined first illumination device/light receiver optical system 2'. Also illumination light from the combined second illumination device/ illumination optical system 3' used for color image observation is used for obtaining measurements in a second scattering angle range. Thus, the present embodiment has the advantage that construction is simplified through the use of a combined illumination optical system used for scattering measurements and an illumination optical system used in color image observation.

In this case as well, the range d0 of the light receiver optical system 2' (namely, the combined first illumination device/ light receiver optical system, since the ranges d0 and d1 are approximately identical) is included in the illumination range d1. In addition, the range d1 is also included in the illumination range d2 which is formed by to the combined second illumination device/illumination optical system 3' used for color image observation. The illumination range d1 of the combined first illumination device/light receiver optical system 2' is established to be included in the illumination range d2 of the combined second illumination device/illumination optical system 3' used for color image observation. Also, as in the case of FIG. 1, the combined second illumination device/ illumination optical system 3' used for color image observation is arranged relative to the combined first illumination device/light receiver optical system 2' so as to satisfy a relationship wherein the angles $\alpha 1$ and $\alpha 2$ defined in the same manner as in FIG. 1 are such that $\alpha 1 < \alpha 2$. In addition, as shown in FIG. 3(a), the detection angles $\theta 1$ and $\theta 2$ of the scattered light are such that $\theta 1$ is in the range 176°-180°, and $\theta 2$ is in the range of 176° or less.

FIG. 4(b) shows the construction of the essential elements of Embodiment 4 with examples of possible modified components of Embodiment 4. The changed components are such that the combined first illumination device/light receiver optical system 2' may be inserted/removed as a probe into the forceps channel of a conventional endoscope, and are constructed so as to be capable of being inserted into the forceps channel 18 at the time of back-scattered light observation. Other construction and methods are the same as in the case of FIG. 4(*a*).

EMBODIMENT 5

Figure 5B:
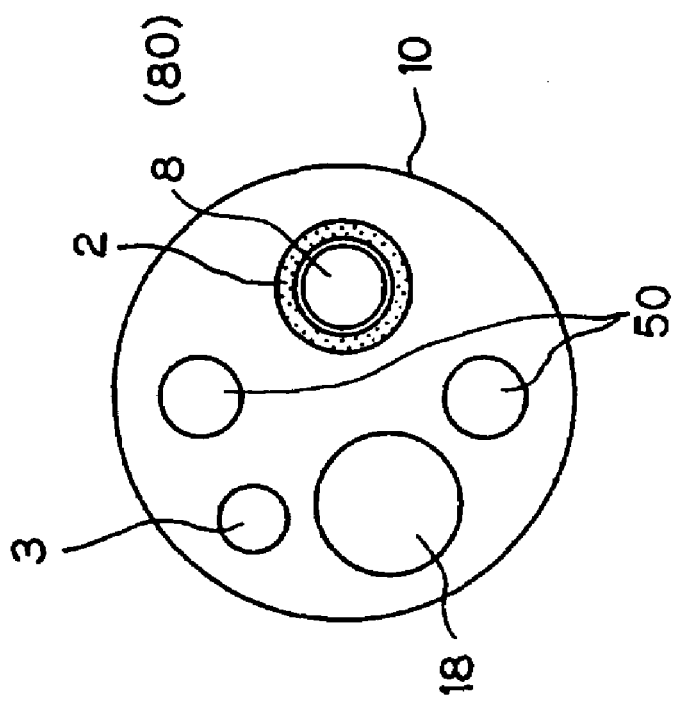
FIGS. 5(a) and 5(b) show the construction of some of the essential components of an endoscope used for obtaining the back-scattering characteristics of an object according to Embodiment 5, with FIG. 5(a) being a side cross-sectional view, and FIG. 5(b) being an axial view of the front part of the endoscope.
Figure 14:
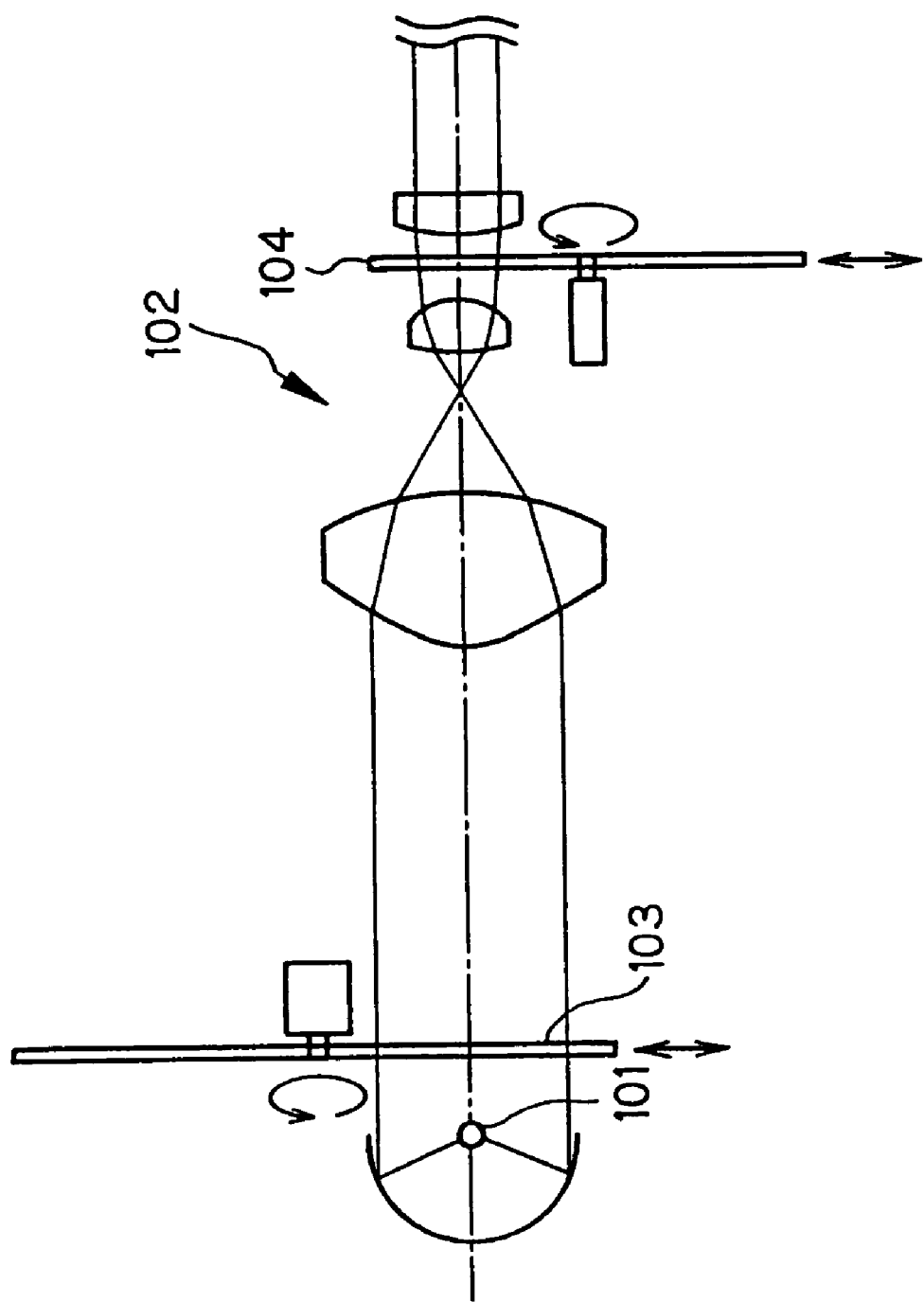
FIG. 14 shows the construction of the light source used in Embodiment 5.
Figure 15A:
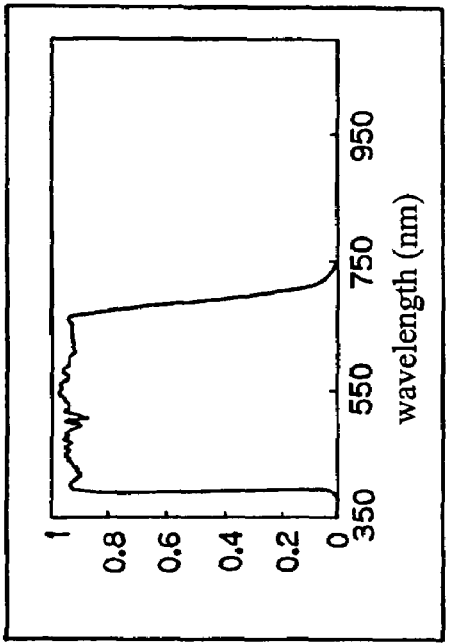
FIGS. 15(a)-15(e) are graphs which show the transmission characteristics of wavelength selective filters that may be arranged in the optical path of the light source according to Embodiment 5 of the present invention.
Figure 15B:
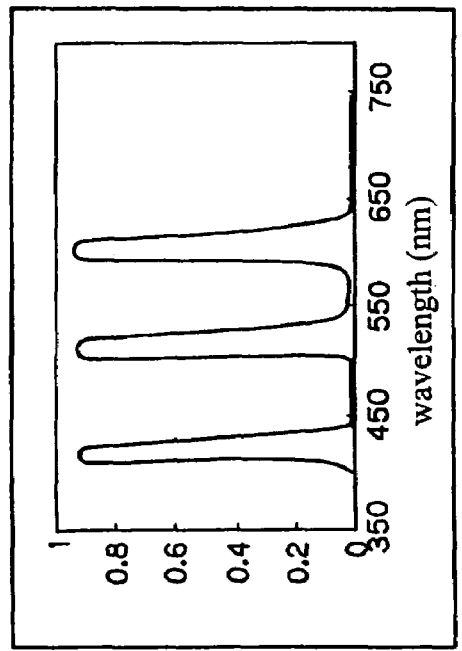
Figure 15E:
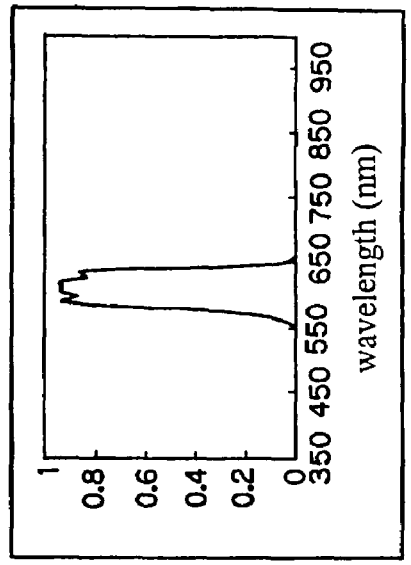
Figure 15D:
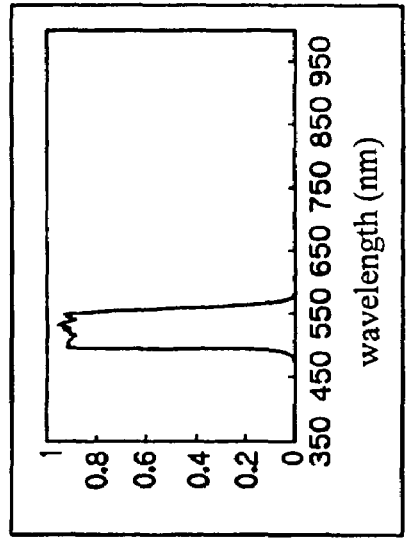
Figure 15C:
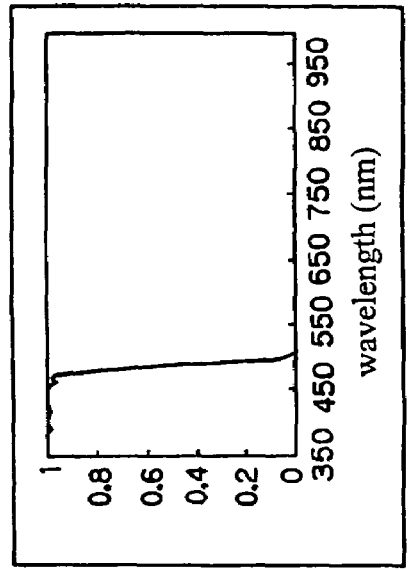

FIG. 5(*a*) is a diagram which shows the construction of the essential elements of an endoscope for observing scattered light from an object, such as living body tissue, according to Embodiment 5. FIG. 5(*b*) is a front surface diagram of the endoscope front end 10. This embodiment is very similar to Embodiment 2 shown in FIG. 2. The construction in this embodiment for the optical switch and the processor is the same as that shown in FIG. 2 for the optical switch 5 and the processor 7, and therefore no further explanation of these components will be given. However, the construction of the light source is different in this embodiment and is shown in FIG. 14, which illustrates a lamp 101, an optical system 102 for guiding light to the optical switch 5 of the illumination optical system, and multiple wavelength selective filters 103 and 104 arranged so as to be freely insertable into and removable from the optical path. Also, a diaphragm, not shown, is used in this embodiment to regulate the intensity of the light.

By changing the combination of the multiple wavelength selective filters 103 and 104, switching between at least the following three modes is possible:

(1) a mode for generating narrow bandwidth illumination light within a visible wavelength region which is used in back-scattered light observations of an object, such as living body tissue;

(2) a mode which generates successive illumination light of blue (B), green (G), and red (R) colors used for observation of the object as well as the peripheral areas to the object; and (3) a mode which generates white illumination light.

For example, in the case of the mode which generates narrow bandwidth illumination light of visible wavelengths used in back-scattered light observations of an object such as living body tissue, a combination is made of filters showing the wavelength characteristics of FIGS. 15(*a*), 15(*c*), 15(*d*) and 15(*e*). The filter shown in FIG. 15(*a*) is fixed in the light flux of the light source 1, and selectively transmits narrow bandwidth lights, each having a half-bandwidth of 10 nm-30 nm. The filters shown in FIGS. 15(*c*), 15(*d*) and 15(*e*) are intermittently inserted into the light flux of the light source 1, and each of them selectively transmit one of the narrow bandwidth lights that transmit through the filter shown in FIG. 15(*a*). In this manner, narrow bandwidth illumination light is generated in the visible wavelength region used in the back-scattered light observation of an object surface such as living body tissue.

In the case of the mode which generates repeated, sequential illumination light in the colors blue (B), green (G), and red (R) used for the observation of object surfaces such as living body tissue as well as the peripheral areas, a combination is made of the filters shown in FIGS. 15(*b*), 15(*c*), 15(*d*) and 15(*e*). The filter shown in FIG. 15(*b*) is fixed in the light flux of the light source 1, and light in the visible wavelength region is selectively transmitted. The filters shown in FIGS. 15(*c*), 15(*d*) and 15(*e*) are intermittently inserted into the light flux of the light source 1, and illumination light is successively generated in the colors blue (B), green (G), and red (R).

In the case of the mode that generates white illumination light, only the filter shown in FIG. 15(*b*) is inserted into the light flux of the light source 1.

In the present embodiment, a first illumination device 2, a second illumination device 3, and an imaging unit 80 that is formed of the objective optical system 8 and an image detector 9 which picks up the image that is formed in the endoscope front end 10 by the objective optical system 8. Furthermore, a separate arrangement is made for an illumination optical system 50, used for observations of color images, that includes an optical fiber bundle 51 and a scattering or diverging optical system 52 arranged at its front end.

Referring again to FIG. 5(*a*), the first illumination device 2 uses flux from an optical fiber 23 that is arranged at the periphery of the imaging unit 80, and the second illumination device 3 uses flux from an optical fiber 31. A negative lens 32 is arranged at the front end of the optical fiber 31. The imaging range d0 of the objective optical system 8 at the surface of the object O is included in the illumination range d1 that corresponds to the region of illumination produced by the first illumination device 2 on the object, as well as in the illumination range d2 which corresponds to the region of illumination produced by the second illumination device 3 on the object. Furthermore, the illumination range d2 is established so as to include the illumination range d1. In addition, the illumination range according to the illumination optical system 50 used for color image observation is established to be included in the illumination range of d2 or greater according to the second illumination device.

In this example, the imaging unit 80 formed of the objective optical system 8 and the image detector 9 makes joint use of the optical system used for color image observation and the optical system used for back-scattered light measurements, and observations are accomplished by means of the following procedures.

First, an endoscope is inserted into a body cavity, and illumination from an illumination optical system used for color image observation provides either time-divided, sequential light beams of blue (B), green (G) and red (R) colors or white light illumination so as to provide ordinary color picture images on a monitor while the front end of the endoscope is led to the object to be observed. Next, the front end of the endoscope is moved into close proximity of the object to be observed, and the position of the endoscope front end is adjusted so that the object is centered within the display area of an ordinary color picture image displayed on the monitor. Next, the illumination mode of the light source is switched and, while a narrow bandwidth light of center wavelength 500 nm or shorter is illuminated for a fixed period of time by the first illumination device 2, imaging is accomplished using back-scattered light from the object received by means of the objective optical system 8 and the image detector 9, thereby obtaining the picture image signal Q1. Next, narrow bandwidth light of center wavelength 500 nm or shorter is illuminated for a fixed period of time by the second illumination device 3, while imaging is accomplished using back-scattered light from the object received by means of the objective optical system 8 and the image detector 9, thereby obtaining the picture image signal Q2. These picture image signals are sent to the processor 7 (FIG. 2) through the signal line 19, and the difference or ratio between the picture image signal Q1 and the picture image signal Q2 is calculated. With the above, aberrations introduced by the objective optical system 8 are minimized by adjusting the position of the endoscope front end in order that the object O is centered when viewing the monitor, as indicated above.

The present embodiment has the advantage that observations and measurements of back-scattered light can be made under optimal conditions by separately establishing the illumination optical system 50 used for color image and the illumination optical systems 2 and 3 used for back-scattering measurements.

In this case as well, the first illumination device 2 and the second illumination device 3 are arranged relative to the objective optical system 8 so as to satisfy a relationship in which the angles α1 and α2 defined in the same manner as in the case of FIG. 2 are such that α1<α2. In addition, as shown in FIG. 3(a), the detection angles θ1 and θ2 of the scattered light are such that θ1 is established in the range of 176°-180°, and θ2 is established to be in the range of 176° or less.

EMBODIMENT 6

Figure 5A:
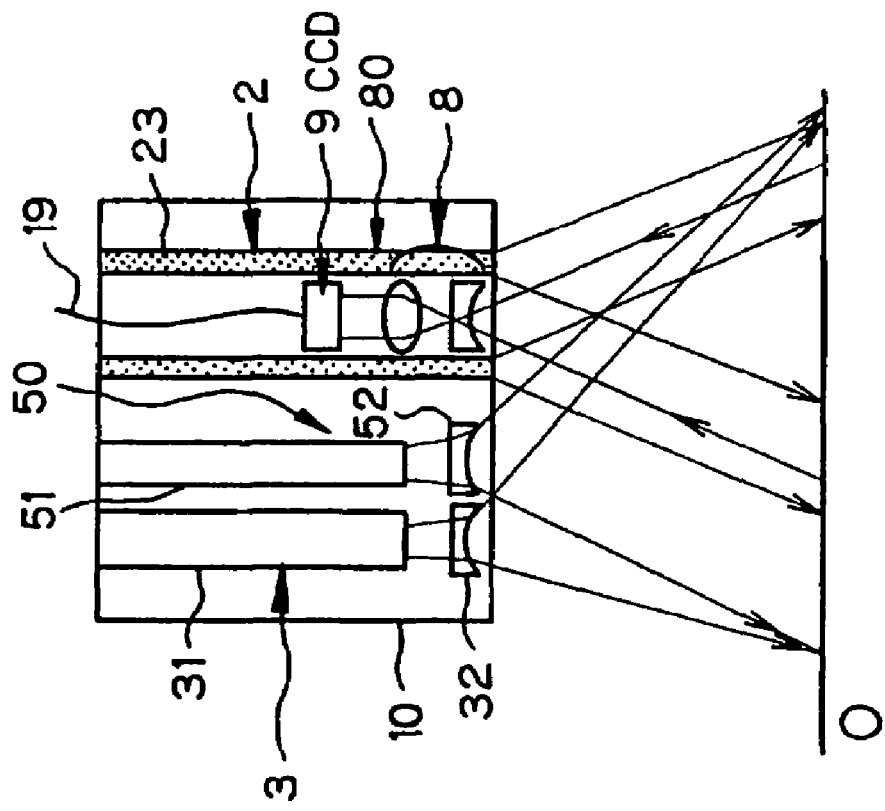
Figure 6A:
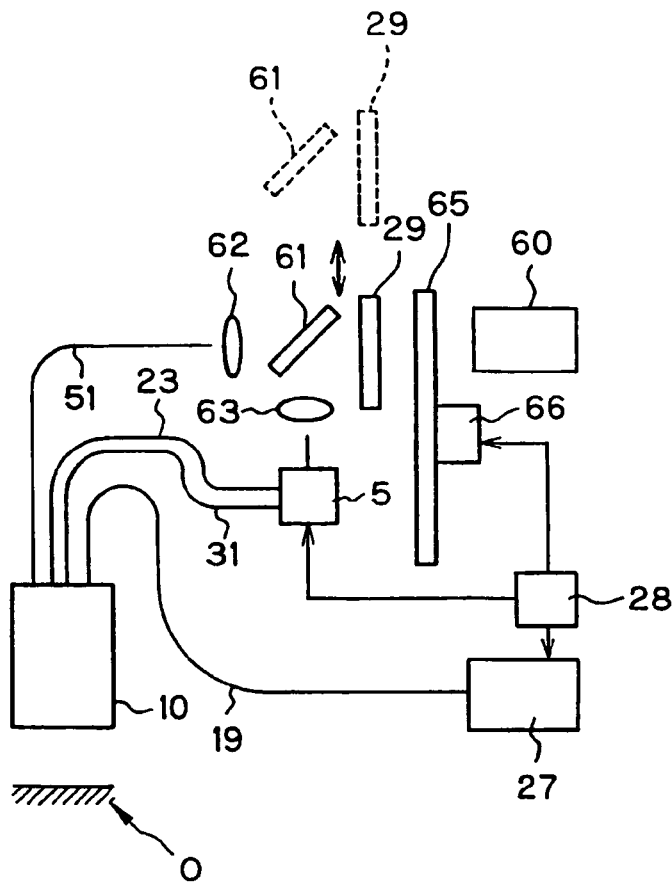
FIGS. 6(a)-6(c) are diagrams used to explain the construction and operation of an endoscope for observation of back-scattered light from an object such as living body tissue according to Embodiment 6 of the present invention.

FIG. 6(a) shows the overall construction of an endoscope for observing scattered light from an object, such as living body tissue, according to Embodiment 6. The embodiment employs the same front end 10 as shown in FIG. 5(a) for Embodiment 5.

Figure 6B:
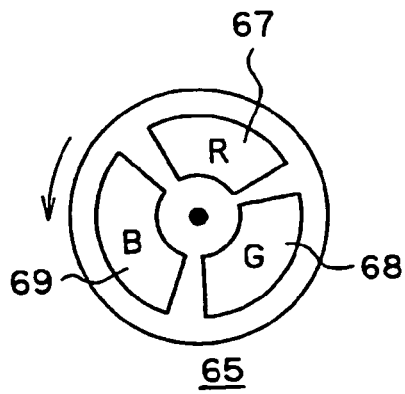

In the present embodiment, a white light source 60 is provided, and an RGB wheel 65 having a construction as shown in FIG. 6(b) is formed by arranging a red R wavelength transmitting filter 67, a green G wavelength transmitting filter 68, and a blue B wavelength transmitting filter 69 within different sectors of the wheel, and with rotational control of the RGB wheel 65 being provided by a motor 66.

As shown in FIG. 6(a), light successively transmitted through the R, G, or B transmitting filters reaches the bandpass filter 29 and the mirror 61, both of which are removable from and insertable into the optical path. In the situation where the bandpass filter 29 and mirror 61 have been removed from the optical path (shown by the broken lines in the drawing), the transmitted light is collected by the light collecting lens 62 and directed to the optical fiber 51 of the illumination optical system 50 used for color image observation. Illumination light that is directed into the optical fiber 51 illuminates the object O which becomes the light diffused by a diffuser optical system at the front end of the illumination optical system 50 used for color image observation. The objective optical system 8 (FIG. 5(a)) which forms an image of the object on the image detector 9, and a picture image signal of the three colors of R, G, B detected by the image detector 9 pass via the signal line 19 to a picture image output device 27 which outputs picture images so that a color image of the object is viewable on a display.

Figure 6C:
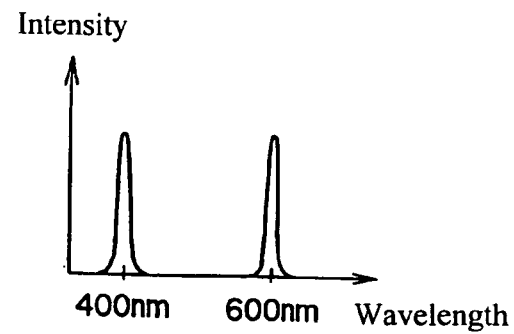

The peak transmission wavelengths of the band pass filter 29, as shown in FIG. 6(c), are centered about, for example, 400 nm for the blue color transmission and 600 nm for the red color transmission. Referring to FIG. 6(a), if the band pass filter 29 and mirror 61 are inserted into the optical path (the situation illustrated with solid lines) then, during the period that the blue transmitting filter 69 of the RGB wheel 65 is in the optical path, narrow bandwidth light having a center wavelength at 400 nm will be passed to the collection lens 63, and this light will illuminate the input end of the optical switch 5. Using the optical switch 5, switching can be accomplished so that, during one period, narrow bandwidth light centered at 400 nm wavelength is incident onto the end of the optical fiber 23 of the first illumination device 2, and during another period narrow bandwidth light centered at 400 nm wavelength is incident onto the end of the optical fiber 31 of the second illumination device 3. During the period in which the second illumination device 3 illuminates light of a narrow bandwidth that is centered at the wavelength 400 nm, imaging using scattered light from the object O is accomplished over the second scattering angle range by means of the objective optical system 8. The image signals are detected by the image detector 9, and picture image signals from the image detector 9 are sent to the processor and picture image output device 27 through the signal line 19.

Figure 7:
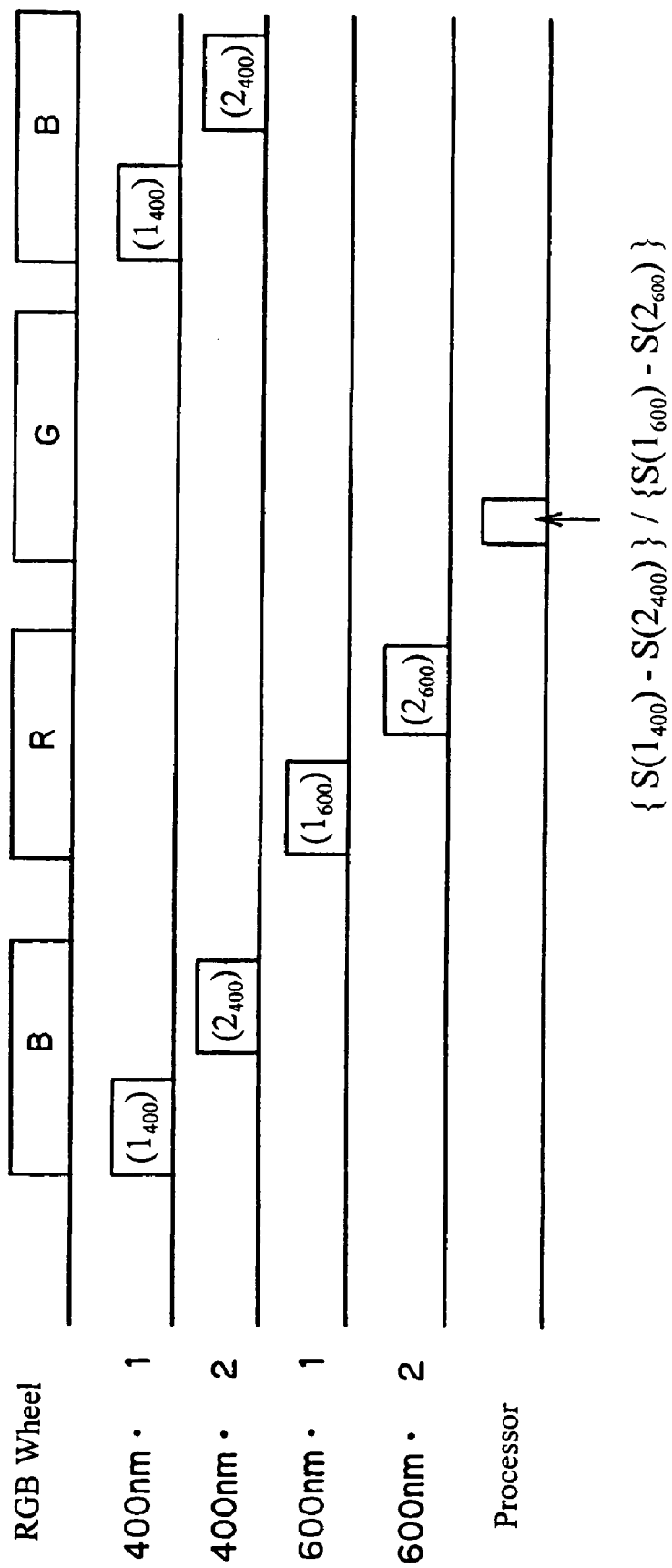
FIG. 7 is a timing chart which shows the operation of an endoscope according to Embodiment 6.

FIG. 7 illustrates the timing of various illuminations and imaging periods. During the period in which the blue transmitting filter 69 of the RGB wheel 65 is in the optical path, imaging is accomplished using back-scattered light of wavelength 400 nm that has been collected in the first range of back-scattering angles, and in the second range of back-scattering angles. In FIG. 7, the imaging period using back-scattered light having a wavelength centered at 400 nm that has been back-scattered within the first range of back-scattering angles is shown as ($1_{400}$), and the imaging period using back-scattered light of wavelength 400 nm in the second range of scattering angles is shown as ($2_{400}$).

Next, in the period in which the red transmitting filter 67 of the RGB wheel 65 is in the optical path, the light of a narrow bandwidth having a center wavelength of 600 nm reaches the light collecting lens 63 by means of the band pass filter 29. Also, by means of the optical switch 5, the light is switched between being incident onto the rear end of the optical fiber 23 of the first illumination device 2 versus being incident onto the rear end of the optical fiber 31 of the second illumination device 3. During the period in which illumination light having a narrow bandwidth centered at a wavelength 600 nm from the first illumination device is incident onto the object, imaging is accomplished using back-scattered light from the object within the first scattering angle range by means of the objective optical system 8. The image detector 9 is used to capture the image. On the other hand, during the period in which illumination light from the second illumination device 3 having a narrow bandwidth centered at a wavelength of 600 nm is incident onto the object, imaging is accomplished by means of the back-scattered light from the object in the second scattering angle range by means of the objective optical system 8. Once again, the image detector 9 is used to capture the image. These picture image signals are then sent to the processor/picture image output device 27. In the period in which the green light transmitting region 68 of the RGB wheel 65 is in the optical path, light from the light source 60 is blocked by the band pass filter 29, and does not reach the first illumination device 2 or the second illumination device 3. During this period, the following calculation is performed by the processor 7, and the result is output to the picture image output device 27:

$$\{S(1_{400})/S(2_{400})\}/\{S(1_{600})/S(2_{600})\} \quad \text{or} \quad \{S(1_{400})/S(2_{400})\}-\{S(1_{600})/S(2_{600})\}$$

where $S(1_{400})$ is an image signal accumulated during the period in which an image is formed using the scattered light of wavelength 400 nm in the first scattering angle range, $S(2_{400})$ is an image signal accumulated during the period in which an image is formed using the scattered light at a wavelength of 400 nm in the second scattering angle range, $S(1_{600})$ is an image signal accumulated during the period in which an image is formed using scattered light at a wavelength of 600 nm in the first scattering angle range, and $S(2_{600})$ is an image signal accumulated during the period in which an image is formed using scattered light at a wavelength of 600 nm in the second scattering angle range.

By this procedure, a value is calculated that corresponds to the size of particles that create the scattering of light and that is independent of the concentration of the particles, and this value, or a signal proportional thereto, is then communicated to the picture image output device 27.

Furthermore, in order to synchronize the imaging timing and the calculation timing, as shown in FIG. 7, control is exercised over the rotation of the motor 66, the switching of the optical switch 5, the obtaining of the picture image signal from the processor/picture image output device 27, and the calculation timing using the controller 28 shown in FIG. 6(a).

EMBODIMENT 7

Figure 8B:
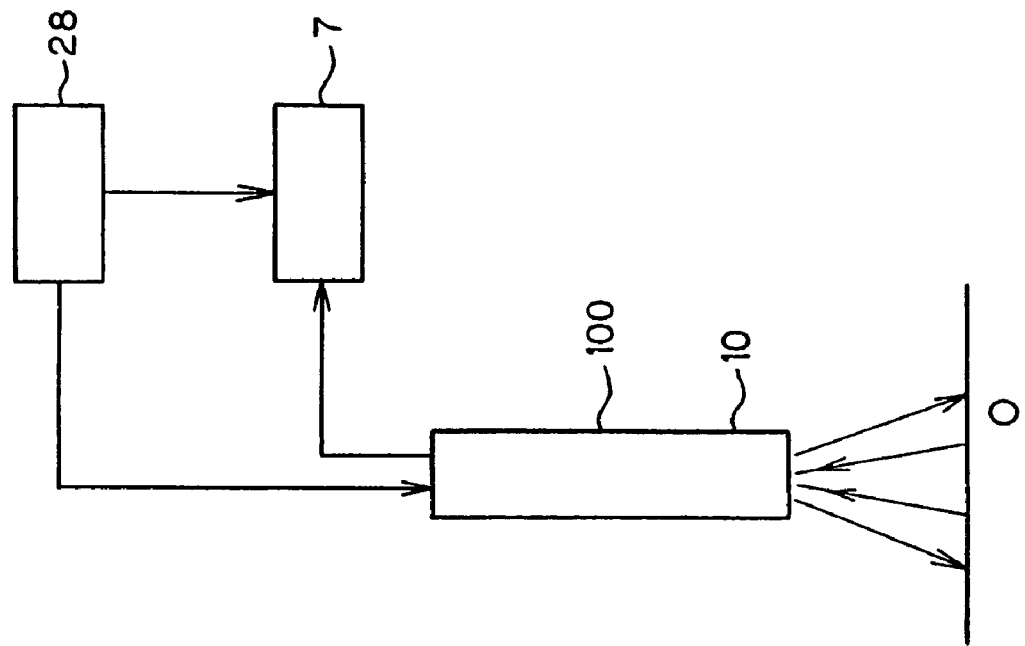
FIGS. 8(a) and 8(b) relate to Embodiment 7 of the present invention, with FIG. 8(a) showing an axial view of the front end of the endoscope according to this embodiment, and FIG. 8(b) being a block diagram illustrating the overall construction of the endoscope according to this embodiment.
Figure 8A:
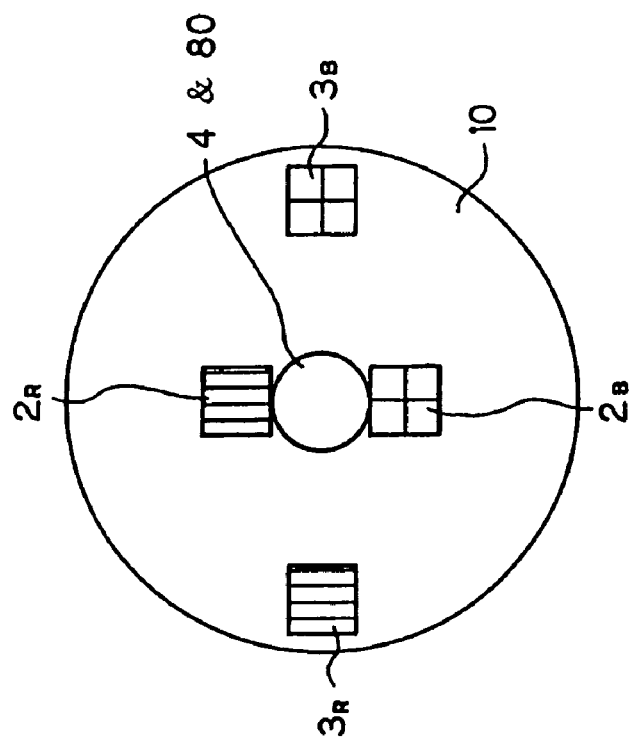

An endoscope for observing scattered light from an object, such as living body tissue, according to the fifth embodiment of the present invention is shown in FIGS. 8(a) and 8(b).

FIG. 8(a) is an axial view of the front end 10 of an endoscope 100 according to this embodiment, and FIG. 8(b) is a block diagram which shows the overall construction of this embodiment. As shown in FIG. 8(a), there is a single light receiver optical system 4 or an imaging unit 80 arranged in the approximate center of the front end 10 of the endoscope. A blue LED $2_B$ which emits light having a wavelength of 400 nm, and a red LED $2_R$ which emits light having a wavelength 600 nm and which serve as first illumination devices are attached at positions which, when the light receiver optical system 4 or the imaging unit 80 is separated a specified distance from the surface of an object O, enables the detection of back-scattered light from the first illumination devices via the object into the light receiver optical system 4 or the imaging unit 80 having scattering angles in the range of 176°-180°. In addition, a blue LED $3_B$ which emits light of wavelength 400 nm and a red LED $3_R$ which emits light of wavelength 600 nm are attached at positions which, when the light receiver optical system or the imaging unit 80 is separated at the specified distance from the surface of the object O, enables the detection of back-scattered light from the second illumination devices via the object into the light receiver optical system 4 or the imaging unit 80 having scattering angles in the range of 176° or less. The light receiver optical system 4 and the imaging unit 80 can be constructed in this embodiment to be identical to those discussed previously concerning Embodiments 1-4, and thus further discussion of these components will be omitted. Furthermore, as discussed above for Embodiment 1, the desired ranges d0, d1, and d2 are the same as discussed previously; thus additional discussion of these parameters will be omitted.

For a given type of device, the controller 28 sequentially and repeatedly energizes the blue LED $2_B$, the blue LED $3_B$, the red LED $2_R$, and the red LED $3_R$ and detects the signals $S1_{400}$, $S2_{400}$, $S1_{600}$, and $S2_{600}$. With the processor 7, as with the case illustrated in FIGS. 7, the above calculation, namely, $\{S(1_{400})/S(2_{400})\}/\{S(1_{600})/S(2_{600})\}$ or $\{S(1_{400})/S(2_{400})\}-\{S(1_{600})/S(2_{600})\}$ is performed, and a value or signal can be obtained that corresponds to the size of the particle independently of the concentrations of the scattering particles.

With this embodiment, by arranging the LEDs $2_R$, $2_B$, $3_R$, $3_B$ used for illumination in the front end part 10 of an endoscope, the selective illumination of the LED's can be controlled electrically and thus there is no need for the optical switch as used in previous embodiments. Thus, the construction according to this embodiment is simplified.

EMBODIMENT 8

Figure 9:
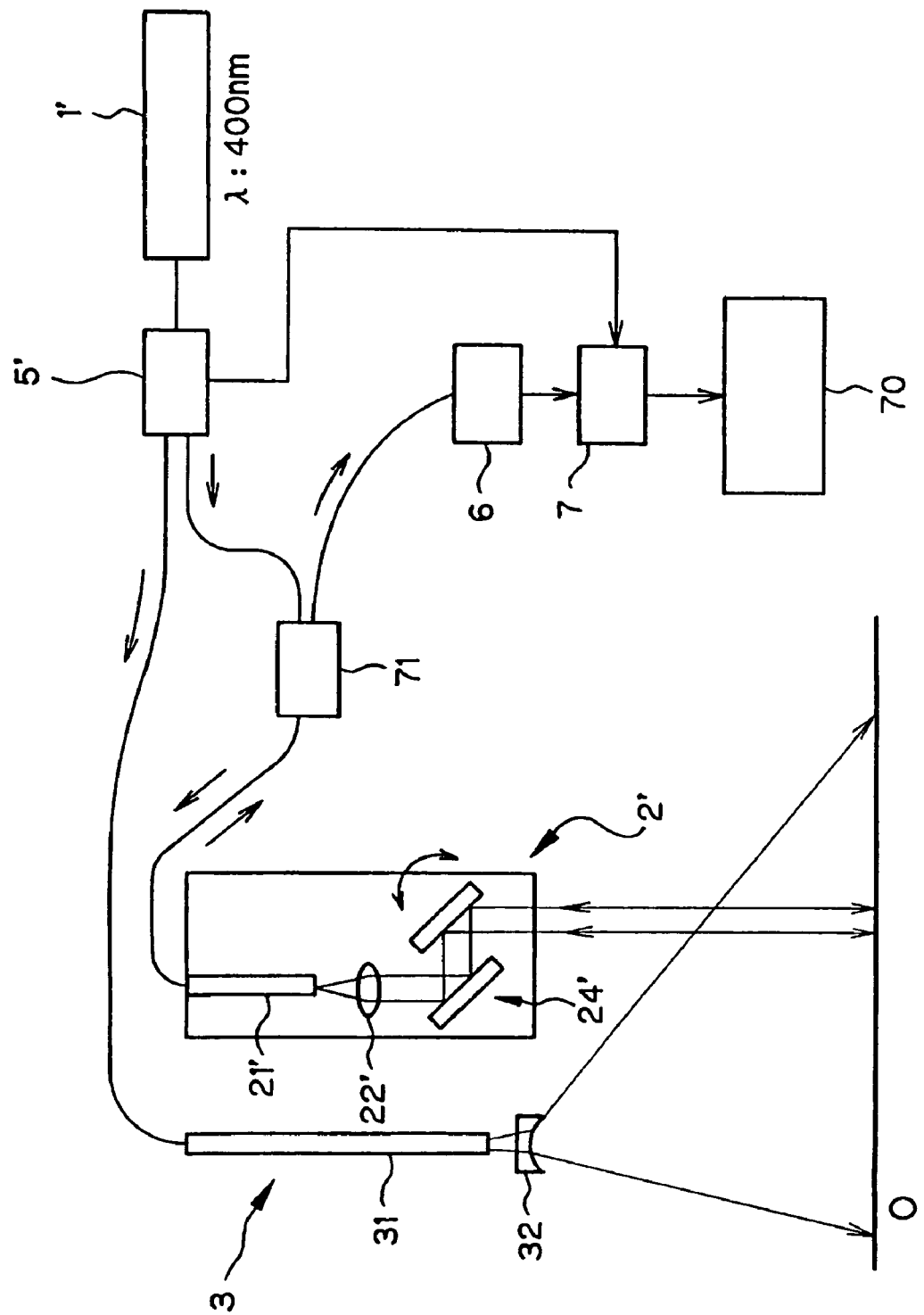
FIG. 9 is a block diagram showing the overall construction of an endoscope according to Embodiment 8 of the present invention.
Figure 10A:
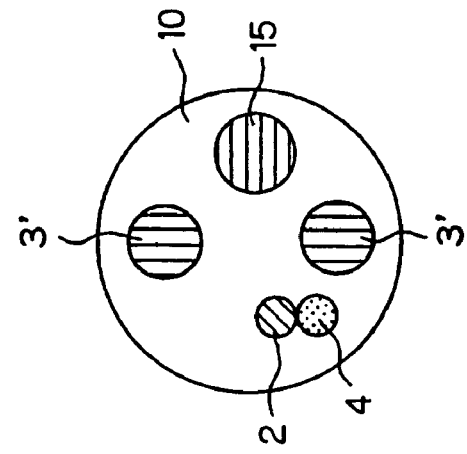
FIGS. 10(a)-10(d) are diagrams which show axial views of the front part of the endoscopes of the present invention and are examples of different arrangements of the components that are possible in the present invention.
Figure 10B:
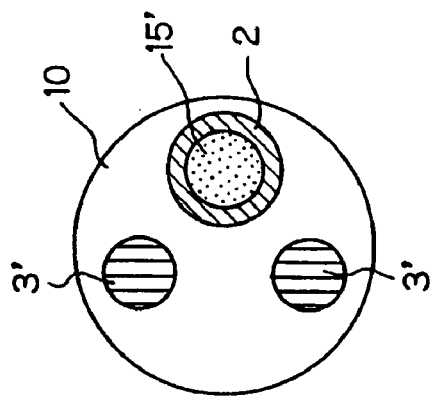
Figure 10C:
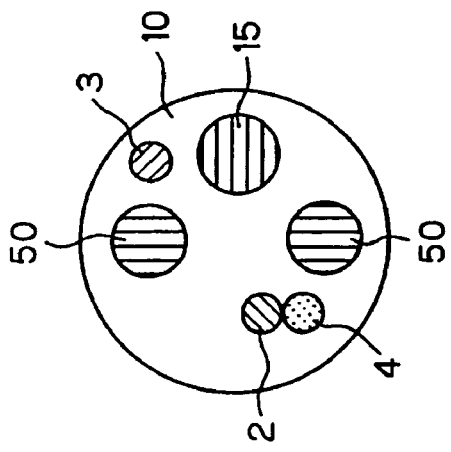
Figure 10D:
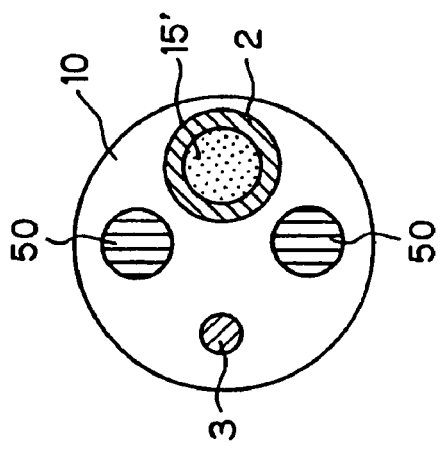

An endoscope for observing scattered light from an object, such as living body tissue, according to the eighth embodiment of the present invention is shown in FIG. 9. This embodiment is an example of observation in which use is made of a laser scan probe. In this embodiment, the first illumination device and the light receiver optical system are combined into one optical system, and are shown in the drawing as a combined first illumination device/light receiver optical system 2'. This combined first illumination device/light receiver optical system 2' is formed of an optical fiber 21', a collimator optical system 22' arranged in front of the optical fiber 21' with its focal point positioned at the end of the optical fiber 21', and a scanning device 24' which two-dimensionally scans the illumination light that has been collimated by the collimator optical system 22'. The second illumination device 3 is formed of an optical fiber 31 having a negative lens 32 arranged at its front end.

In this embodiment, the laser 1' generates coherent light having a wavelength, for example, of 400 nm that passes through the optical path switching device 5', and is selectively led either to the combined first illumination device/light receiver optical system 2' or to the second illumination device 3. The illumination light which is directed to the combined first illumination device/light receiver optical system 2' first passes through a circulator 71 and then is directed to the rear end of the optical fiber 21'. After this light has been collimated by the collimator optical system 22' it is scanned over the surface of the object O by means of the scanning device 24'. The light back-scattered by the object O passes through the same scanning device 24' as well as through the collimator optical system 22', so as to be directed into the front end of the optical fiber 21'. This light then passes through the circulator 71, is separated from the illumination light, and then is detected by the detector 6.

By synchronizing and displaying the detector signal with the scanning position of the scanning device 24', a picture image of the surface of the object O can be displayed on the picture image output device 70. In addition, by means of the processor 7 making the calculation as detailed above in discussing Embodiment 6, information relating to the size of the particles can be obtained.

According to this embodiment, by controlling the scanning range of the scanning device 24', or by omitting data of picture image regions not of interest, signal or picture images not of interest can be avoided, thereby enabling a viewer's attention to be fully focused on the signal or picture of interest.

In addition, by changing the form of this embodiment in the same manner as done when referring to FIG. 4(b) of Embodiment 4, the combined first illumination device/light receiver optical system 2' can be inserted into the forceps channel of a conventional endoscope, using the combined first illumination device/light receiver optical system 2' as a probe, and with a construction by which it is removable and is made so as to be inserted into the forceps channel only at the time of the scattering measurement observation.

As is clear from the explanation of this embodiment, in the case where the endoscope is equipped with elements or units used for back-scattered light observations of an object such as living body tissue according to the present intervention, an illumination optical system used for conventional observation and an illumination optical system used for scattering measurements can be used in combination or in an independent arrangement. In particular, an endoscope can be provided wherein a second illumination device can be used jointly or used in an independent arrangement. Furthermore, the objective optical system used for conventional observation, the light receiver optical system used for scattering measurements or an imaging optical system can be used in combination or in an independent arrangement. Therefore, different arrangements of these components are shown in FIGS. 10(a)-10(d). In these figures, 2 represents a first illumination device used for independent scattering measurements, 3 represents a second illumination device used for independent scattering measurements, 3' represents a combined second illumination device/illumination optical system used for color image observation, 4 represents a light receiver optical system used for independent scattering measurements, 50 represents an illumination optical system used for independent color image observation, 15 represents an objective optical system used for color image observation, and 15' represents a combined objective optical system used for ordinary observation/imaging optical system used for scattering measurements. Each of FIGS. 10(*a*)-10(*d*) shows an axial view of the front end of an endoscope for observing scattered light from an object, such as living body tissue.

FIG. 10(*a*) illustrates an arrangement of illumination optical systems 50, 50 used for independent color image observation, a first illumination device 2 used for independent scattering measurements, a second illumination device 3 used for independent scattering measurements, an objective optical system 15 used for color image observation, and a light receiver optical system 4 used for independent scattering measurements.

FIG. 10(*b*) illustrates an arrangement of a first illumination device 2 used for independent scattering measurements, a combined second illumination device/illumination optical system used for color image observation 3', 3', a light receiver optical system used for independent scattering measurements 4, and an objective optical system used for color image observation 15.

FIG. 10(*c*) illustrates an arrangement of illumination optical systems 50, 50 used for independent color image observations, a first illumination device 2 used for independent scattering measurements, a second illumination device 3 used for independent scattering measurements, as well as a combined objective optical system 15' used for color image observation/imaging optical system used for scattering measurements.

FIG. 10(*d*) illustrates an arrangement of a first illumination device 2, a combined second illumination device/illumination optical system used for color image observation 3', 3', and a combined objective optical system used for ordinary observation/imaging optical system used for scattering measurement 15'.

METHOD

The method of the present invention uses an optical apparatus that is inserted into a cavity of a living body to observe light scattered by living tissue. The optical apparatus has a front end portion that is provided with a light reception window, a first illumination window, and a second illumination window that is arranged farther from the light reception window than is the first illumination window. The method comprises the following steps, performed in the indicated order:

(a) using the above-described optical apparatus, emitting a first narrow bandwidth illumination light that is included in a visible wavelength region for a fixed duration of time from the first illumination window to the living body tissue, and concurrently receiving through the reception window light of the first narrow bandwidth that has been back-scattered from the living body tissue;

(b) using the above described optical apparatus, emitting a second narrow bandwidth illumination light that is included in a visible wavelength region for a fixed duration of time from the second illumination window to the living body tissue but in different timing from that of the illumination light that is emitted from the first illumination window, and concurrently receiving through the reception window, light of the second narrow bandwidth that has been back-scattered from the living body tissue; and (c) calculating one of a difference of the scattered light intensities received in step (a) versus step (b) or the ratio of the intensity of the scattered light received in step (a) divided by the intensity of the scattered light received in step (b).

The illumination lights in steps (a) and (b) above each has a narrow bandwidth centered at a wavelength of 500 nm or less, and the method may additionally include the following steps:

(d) emitting a separate, narrow bandwidth illumination light that is in the visible wavelength region and has a different wavelength from the first narrow band illumination light for a fixed duration of time from the first illumination window onto the object, and concurrently receiving through the light receiver window light that has been scattered by the object;

(e) emitting a separate, narrow bandwidth illumination light that is in the visible region and has a different wavelength from the second narrow band illumination light for a fixed duration of time from the second illumination window onto the object, and concurrently receiving through the light receiving window light that has been scatted by the object; and (f) calculating the difference in intensities of the scattered light received in step (d) versus step (e), or calculating a ratio of the intensities of the scattered light received in steps (d) and (e).

In these methods, the wavelength of the first narrow band illumination in (a) and that of the second illumination in (b) may be the same wavelengths and, also, the narrow band illuminations in (d) and (e) may be the same wavelengths.

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. An endoscope apparatus having an insertable portion for examining an object within a living body using scattered light, said endoscope apparatus comprising:
   a light source;
   a first illumination device that directs light from the light source and illuminates the object from the insertable portion of the endoscope apparatus with a first light beam having a center ray and a first wavelength;
   a second illumination device that directs light from the light source and illuminates the object from the insertable portion of the endoscope apparatus with a second light beam having a center ray and a second wavelength;
   a detector;
   a light receiver optical system having a field of view and an optical axis, and that receives light from the first and second illumination devices that has been back-scattered from the object and guides it to the detector; and
   a processor that calculates a value that corresponds to the size of particles of an object that scatter light;
   wherein
   at least two of the first illumination device, the second illumination device, and the light receiver optical system include a positive or negative lens having a lateral offset relative to an optical axis of light that is incident onto the positive or negative lens;
   the center ray of the first light beam and the center ray of the second light beam intersect the optical axis of the light receiver optical system at substantially the same point; and
   the first illumination device and the second illumination device are arranged so that the following condition is satisfied $\alpha 1 < \alpha 2$ where
   $\alpha 1$ is the angle formed by the optical axis of the light receiver optical system and the center ray of the first light beam, which is defined as a line that is included in the first light beam and is substantially in the center of the bundle of rays that are emitted from the first illumination device and intersect at a point where the optical axis of the light receiver optical system intersects the surface of an object; and α2 is the angle formed by the optical axis of the light receiver optical system and the center ray of the second light beam, which is defined as a line that is included in the second light beam and is substantially in the center of the bundle of rays that are emitted from the second illumination device and intersect at a point where the optical axis of the light receiver optical system intersects the surface of an object.

2. The endoscope apparatus according to claim 1, wherein:
the region of the object that is illuminated by the first illumination device includes the field of view of the light receiver optical system; and
the first illumination device and the second illumination device are arranged relative to the light receiver optical system so that the illumination range of the second illumination device includes the illumination range of the first illumination device.

3. The endoscope apparatus according to claim 2, and further comprising:
an objective optical system that forms an image of the object separately from the image formed with the scattered light; and
an image detector that is arranged at the image surface formed by the objective optical system for capturing images.

4. The endoscope apparatus according to claim 3, wherein the second illumination device also serves as an illumination device for an observer to view the object in the same manner as with a conventional endoscope.

5. The endoscope apparatus according to claim 4, and further comprising: a light source device which includes a light emission source and a plurality of wavelength selection filters that are insertable into and removable from a light path emitted from the light emission source;
wherein
a light source device is provided with an operation mode which creates narrow bandwidth illumination light in a visible wavelength region used in the back-scattered light observation of the object, and at least one of the following operation modes:
a mode which creates successive illumination light of blue B, green G, and red R colors; and
a mode which creates white illumination light.

6. The endoscope apparatus according to claim 2, wherein:
the first illumination device and the light receiver optical system share a common optical axis.

7. The endoscope apparatus according to claim 6, wherein the light receiver optical system includes a collimator optical system.

8. The endoscope apparatus according to claim 2, and further comprising an optical switch that leads the illumination light from the light source to either the first illumination device or the second illumination device.

9. The endoscope apparatus according to claim 8, wherein:
the light source comprises multiple wavelength selection filters that are arranged to be freely insertable into and removable from the optical path, and
an operation mode is provided which creates narrow bandwidth illumination light in the visible wavelength region that is used in the back-scattered light observation of the object, and at least one of the following operation modes is also provided:
a mode which creates successive illumination light of blue B, green G, and red R colors; and
a mode which creates white illumination light.

10. The endoscope apparatus according to claim 2, wherein the first illumination device and the second illumination device direct light from the light source and illuminate the object with light having wavelengths of 500 nm or shorter.

11. The endoscope apparatus according to claim 2, wherein
the first illumination device directs light from the light source and illuminates the object with at least two narrow bandwidth visible lights having different center wavelengths,
the second illumination device directs light from the light source and illuminates the object with at least two narrow bandwidth visible lights having different center wavelengths; and
the calculation by the processor is accomplished by using the detected signals being output from a detector when said at least two narrow bandwidth lights illuminate the sample.

12. The endoscope apparatus according to claim 11, wherein
the processor performs the following calculation (signal I/signal II) or (signal I−signal II)

where
signal I is obtained using narrow bandwidth illumination having a wavelength of 500 nm or shorter that illuminates the object, and is the difference between the signal having a wavelength of 500 nm or shorter that is detected at the time of illumination of the first illumination device versus the signal having a wavelength of 500 nm or shorter that is detected at the time of illumination of the second illumination device, and
signal II is obtained using narrow bandwidth illumination having a wavelength of 500 nm or greater that illuminates the object, and is the difference between the signal having a wavelength of 500 nm or greater that is detected at the time of illumination of the first illumination device versus the signal having a wavelength of 500 nm or greater that is detected at the time of illumination of the second illumination device.

13. The endoscope apparatus as disclosed in claim 2, wherein the first illumination device serves as the light receiver optical system, and the combined first illumination device/light receiver optical system includes a collimator optical system.

14. The endoscope apparatus according to claim 1, wherein the first illumination device and the second illumination device are arranged relative to the optical axis of the light receiver optical system so that:
when the object is illuminated by the first illumination device, α1 is within the range of 0°-4°; and
when the object is illuminated by the second illumination device, α2 is within the range of 4° or more.

15. The endoscope apparatus according to claim 1, wherein the light receiver optical system includes a collimator optical system.

16. The endoscope apparatus according to claim 1, wherein the first illumination device and the second illumination device illuminate the object in different timing for detecting back-scattered light from living body tissue.

17. The endoscope apparatus according to claim 1, wherein the processor calculates one of:
(a) the difference of a first signal being output from the detector when an object is illuminated by the first illumination device versus a second signal being output from the detector when the object is illuminated by the second illumination device, or
(b) a ratio of the first signal and the second signal.

18. An endoscope apparatus having an insertable portion for examining an object within a living body using scattered light, said endoscope apparatus comprising:

a light source;

a first illumination device that directs light from the light source and illuminates the object from an insertable portion of the endoscope apparatus with a first light beam having a center ray and a first wavelength;

a second illumination device that directs light from the light source and illuminates the object from an insertable portion of the endoscope apparatus with a second light beam having a center ray and a second wavelength;

an objective optical system having an optical axis;

an image pickup device that receives an image formed by the objective optical system;

a processor that calculates a difference of a first image signal being output from the image pickup device when an object is illuminated by the first illumination device versus a second image signal being output from the image pickup device when the object is illuminated by the second illumination device, or that calculates a ratio of the first image signal divided by the second image signal;

wherein at least two of the first illumination device, the second illumination device, and the light receiver optical system include a positive or negative lens having a lateral offset relative to an optical axis of light that is incident onto the positive or negative lens;

the first and second illumination devices are so arranged that a center line of a light beam emitted from the first illumination device and a center line of a light beam emitted from the second illumination device intersect at substantially the same point on said optical axis;

the first and second illumination devices are so arranged that the angle formed by the illumination light at the time of illumination by the first illumination device and the scattered light detected from the object by the light receiver optical system, that is, at the angle 180° minus α1, is within the range of 176°-180°, and that the angle of the illumination light that is incident onto the object at the time of illumination by the second illumination device and the scattered light detected from the object with the light receiver optical system, that is, at the angle 180°minus α2, is greater than or equal to 176°; and the first illumination device and the second illumination device are arranged so that the following condition is satisfied

α1<α2 where

α1 is the angle formed by the optical axis of the image pickup device and the center ray of the first light beam, which is defined as a line that is included in the first light beam and is substantially in the center of the bundle of rays that are emitted from the first illumination device and intersect at a point where the optical axis of the objective optical system intersects the surface of an object; and α2 is the angle formed by the optical axis of the image pickup device and the center ray of the center light beam, which is defined as a line that is included in the second light beam and is substantially in the center of the bundle of rays that are emitted from the second illumination device and intersect at a point where the optical axis of the objective optical system intersects the surface of an object.

19. The endoscope apparatus according to claim 18, wherein the wavelengths of the illumination lights from the first illumination device and the second illumination device are 500 nm or shorter.

20. The endoscope apparatus according to claim 19, wherein the second illumination device is formed as a combined second illumination device/illumination optical system.

21. The endoscope apparatus according to claim 18, wherein the first illumination device and the second illumination device are arranged relative to the objective optical system so that the illumination range of the object using the first illumination device includes the light reception range of the objective optical system, and the illumination range of the object using the second illumination device includes the illumination range of the first illumination device.

22. The endoscope apparatus according to claim 21, wherein the second illumination device is formed as a combined second illumination device/illumination optical system.

23. The endoscope apparatus according to claim 21, and further comprising:

a light source device which includes a light emission source and a plurality of wavelength selection filters that are insertable into and removable from a light path emitted from the light emission source;

wherein a light source device is provided with an operation mode which creates narrow bandwidth illumination light in a visible wavelength region used in the back-scattered light observation of the object, and at least one of the following operation modes:

a mode which creates successive illumination light of blue B, green G, and red R colors; and a mode which creates white illumination light.

24. The endoscope apparatus according to claim 18, wherein the first illumination device and the second illumination device illuminate the object in different timing for detecting back-scattered light from living body tissue.

25. An endoscope apparatus having an insertable portion for examining an object within a living body using scattered light, said endoscope apparatus comprising:

a light source;

a first illumination device that directs light from the light source and illuminates the object from the insertable portion of the endoscope apparatus with a first light beam having a center ray and a first wavelength;

a second illumination device that directs light from the light source and illuminates the object from the insertable portion of the endoscope apparatus with a second light beam having a center ray and a second wavelength;

an objective optical system having an optical axis;

an image pickup device having an optical axis that receives an image formed by the objective optical system; and a processor that calculates the difference between a first image signal being output from the image pickup device when the object is illuminated by the first illumination device versus a second image signal being output from the image pickup device when the object is being illuminated by the second illumination device, or that calculates the ratio of said first image signal divided by said second image signal;

wherein at least two of the first illumination device, the second illumination device, and the light receiver optical system include a positive or negative lens having a lateral offset relative to an optical axis of light that is incident onto the positive or negative lens;

the first illumination device and the second illumination device are so arranged that a center line of a light beam emitted from the first illumination device and a center line of a light beam emitted from the second illumination device intersect at substantially the same point on said optical axis;

the first illumination device and the second illumination device are arranged so that the following condition is satisfied $$\alpha 1 < \alpha 2$$

where $\alpha 1$ is the angle formed by the optical axis of the image pickup device and the center ray of the first light beam, which is defined as a line that is included in the first light beam and is substantially in the center of the bundle of rays that are emitted from the first illumination device and intersect at a point where the optical axis of the image pickup device intersects the surface of an object;

$\alpha 2$ is the angle formed by the optical axis of the image pickup device and the center ray of the second light beam, which is defined as a line that is included in the second light beam and is substantially in the center of the bundle of rays that are emitted from the second illumination device and intersect at a point where the optical axis of the image pickup device intersects the surface of an object; and the first light beam and the second light beam each have a narrow bandwidth centered in the wavelength region of 500 nm or shorter.

26. The endoscope apparatus according to claim 25, wherein the first illumination device and the second illumination device illuminate the object in different timing for detecting back-scattered light from living body tissue.

* * * * *